(12) United States Patent
Pierce

(10) Patent No.: US 8,679,076 B2
(45) Date of Patent: Mar. 25, 2014

(54) METHOD AND APPARATUS FOR HARVESTING AND DISPENSING A FIBRIN CLOT

(76) Inventor: Javin C. Pierce, Stowe, VT (US)

(*) Notice: Subject to any disclaimer, the term of this patent is extended or adjusted under 35 U.S.C. 154(b) by 423 days.

(21) Appl. No.: 12/816,135

(22) Filed: Jun. 15, 2010

(65) Prior Publication Data

US 2011/0092919 A1    Apr. 21, 2011

Related U.S. Application Data

(63) Continuation-in-part of application No. 12/749,282, filed on Mar. 29, 2010, which is a continuation-in-part of application No. 12/714,047, filed on Feb. 26, 2010, now abandoned.

(60) Provisional application No. 61/164,212, filed on Mar. 27, 2009, provisional application No. 61/155,842, filed on Feb. 26, 2009, provisional application No. 61/268,670, filed on Jun. 15, 2009.

(51) Int. Cl.
*A61M 5/00* (2006.01)
*C12M 1/00* (2006.01)
*C12N 5/078* (2010.01)

(52) U.S. Cl.
USPC .......... 604/264; 435/283.1; 435/325

(58) Field of Classification Search
USPC ........ 604/246, 264; 435/283.1, 325; 210/782, 210/776
See application file for complete search history.

(56) References Cited

U.S. PATENT DOCUMENTS

| | | | |
|---|---|---|---|
| 3,153,496 A | 10/1964 | Johnson | |
| 3,828,987 A | 8/1974 | Drummond et al. | |
| 4,646,738 A | 3/1987 | Trott | |
| 4,674,500 A | 6/1987 | DeSatnick | |
| 4,790,819 A | 12/1988 | Li et al. | |
| 5,118,428 A | 6/1992 | Sand et al. | |
| 5,432,084 A * | 7/1995 | Brubaker | 435/287.2 |
| 5,695,507 A * | 12/1997 | Auth et al. | 606/159 |
| 5,864,017 A * | 1/1999 | Brubaker | 530/380 |
| 2003/0069601 A1 | 4/2003 | Nowakowski et al. | |
| 2004/0037819 A1* | 2/2004 | Pascher et al. | 424/93.21 |
| 2005/0240146 A1* | 10/2005 | Nash et al. | 604/35 |
| 2006/0243676 A1* | 11/2006 | Swift et al. | 210/782 |
| 2009/0236297 A1 | 9/2009 | Dorian et al. | |
| 2011/0034851 A1* | 2/2011 | Pierce et al. | 604/6.01 |

OTHER PUBLICATIONS

Arnoczky, S.P., et al., Meniscal Repair Using an Exogenous Fibrin Clot—An Experimental Study in Dogs, The Journal of Bone and Joint Surgery, 1988, pp. 1209-1217.

Henning, C.E., et al., Vascularity for Healing of Meniscus Repairs, Arthroscopy: The Journal of Arthroscopic and Related Surgery, 1987, pp. 13-18, vol. 3, No. 1, Raven Press.

* cited by examiner

*Primary Examiner* — Emily Schmidt
*Assistant Examiner* — Michael J Anderson
(74) *Attorney, Agent, or Firm* — Pandiscio & Pandiscio

(57) ABSTRACT

Apparatus for extracting fibrin from blood so as to form a fibrin clot, the apparatus comprising:
 a vessel for holding drawn blood;
 a lid for selectively closing off the vessel; and
 a precipitator connected to the lid for engaging the drawn blood contained within the vessel and acting as a focal point for the precipitation of fibrin clot.

19 Claims, 29 Drawing Sheets

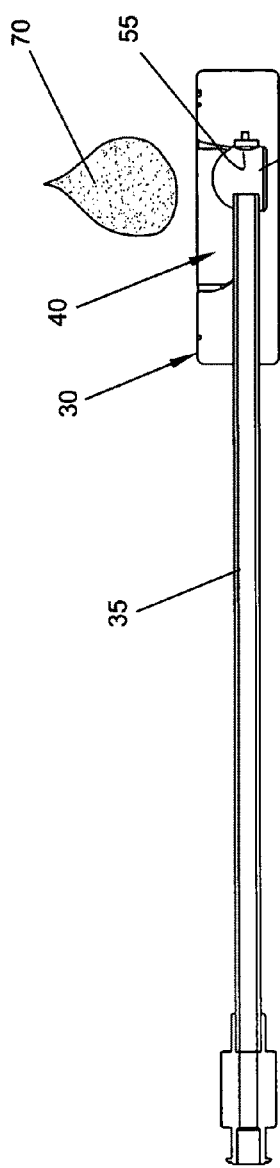
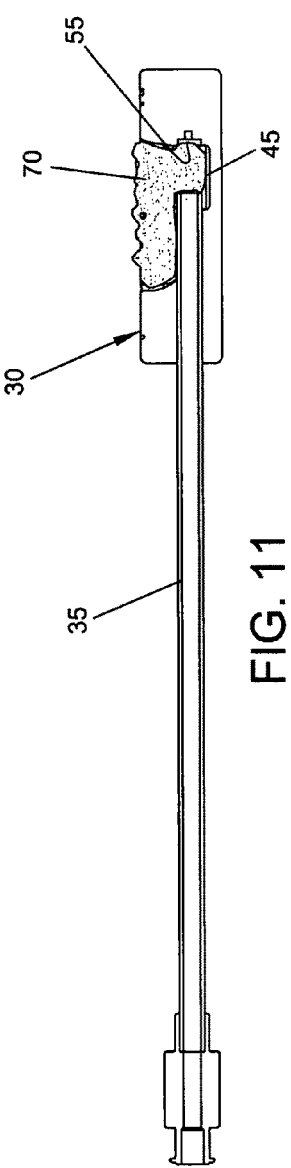
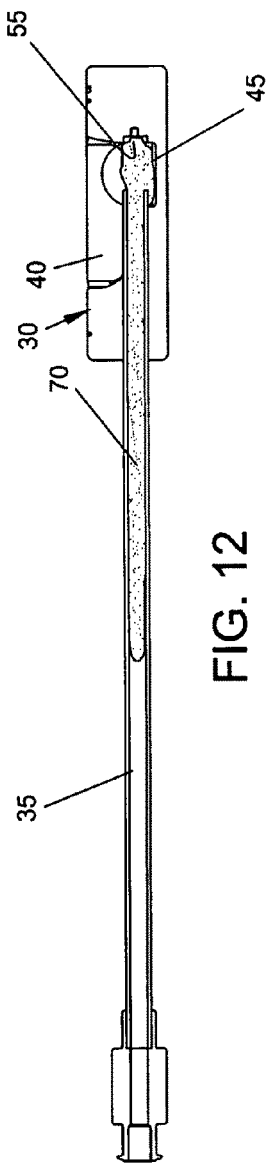
FIG. 10
FIG. 11
FIG. 12

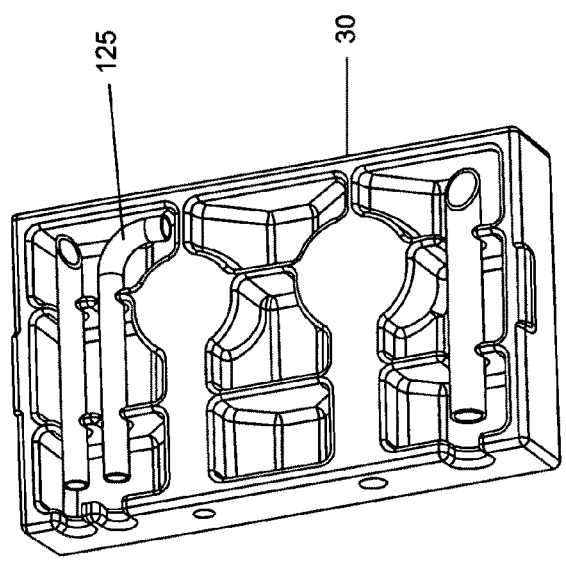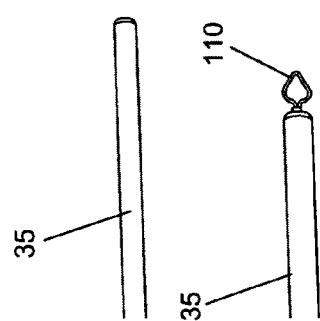
FIG. 20

METHOD AND APPARATUS FOR HARVESTING AND DISPENSING A FIBRIN CLOT

REFERENCE TO PENDING PRIOR PATENT APPLICATIONS

This patent application:

(1) is a continuation-in-part of pending prior U.S. patent application Ser. No. 12/749,282, filed Mar. 29, 2010 by Javin C. Pierce et al. for SYSTEM FOR HARVESTING AND DISPENSING A FIBRIN CLOT, which patent application in turn claims benefit of prior U.S. Provisional Patent Application Ser. No. 61/164,212, filed Mar. 27, 2009 by Javin C. Pierce et al. for SYSTEM FOR HARVESTING AND DISPENSING BLOOD CLOT;

(2) is a continuation-in-part of pending prior U.S. patent application Ser. No. 12/714,047, filed Feb. 26, 2010 now abandoned by Javin C. Pierce et al. for SYSTEM FOR HARVESTING AND DISPENSING BLOOD CLOT, which patent application in turn claims benefit of prior U.S. Provisional Patent Application Ser. No. 61/155,842, filed Feb. 26, 2009 by Javin C. Pierce et al. for SYSTEM FOR HARVESTING AND DISPENSING BLOOD CLOT; and (3) claims benefit of pending prior U.S. Provisional Patent Application Ser. No. 61/268,670, filed Jun. 15, 2009 by Javin C. Pierce for SYSTEM FOR HARVESTING AND DISPENSING BLOOD CLOT.

The five (5) above-identified patent applications are hereby incorporated herein by reference.

FIELD OF THE INVENTION

This invention relates to surgical methods and apparatus in general, and more particularly to a novel method and apparatus for harvesting a fibrin clot and depositing that fibrin clot into a wound site during a surgical procedure.

BACKGROUND OF THE INVENTION

The creation of a hematoma or fibrin clot is an initial and important phase in wound repair. The fibrin clot provides a matrix scaffold as well as a chemotactic stimulus to the various cellular elements involved in wound repair. The fibrin clot is typically a naturally-occurring response to an injury to vascularized tissue.

However, this fibrin clotting is frequently absent in injuries to certain types of tissue which are not highly vascularized, e.g., the meniscus of the knee. Clinical and experimental observations have shown, however, that in many cases the insertion of a fibrin clot into the point of injury in such tissue will aid in the healing process. Furthermore, it has also been found that the insertion of a fibrin clot into other settings (e.g., the point of attachment of a graft ligament to a host bone) can also enhance the speed and integrity of the ligament attachment process.

In practice, it can be time consuming and inconvenient to harvest a fibrin clot and deposit that fibrin clot into a wound site during a surgical procedure.

Thus there is a need for a new and improved method and apparatus for harvesting a fibrin clot and depositing that fibrin clot into a wound site during a surgical procedure.

SUMMARY OF THE INVENTION

The present invention provides a new and improved method and apparatus for harvesting a fibrin clot and depositing that fibrin clot into a wound site during a surgical procedure.

In one preferred form of the invention, there is provided apparatus for extracting fibrin from blood so as to form a fibrin clot, the apparatus comprising:

a vessel for holding drawn blood;

a lid for selectively closing off the vessel; and a precipitator connected to the lid for engaging the drawn blood contained within the vessel and acting as a focal point for the precipitation of fibrin clot.

In another preferred form of the invention, there is provided apparatus for cutting a segment of fibrin clot from a larger mass of fibrin clot and dispensing the cut segment of fibrin clot to a desired location, the apparatus comprising:

a clot preparation block including a chamber for receiving a mass of fibrin clot; and a coring tube comprising:

a hollow tube having a window formed therein; and an inner member having an open distal chamber aligned with the window;

the hollow tube being sized to fit within the chamber of the clot preparation block.

In another preferred form of the invention, there is provided apparatus for dispensing a fibrin clot at a selected location, the apparatus comprising:

a skewer for piercing fibrin clot;

a hollow plunger slidably received on the skewer for removing the fibrin clot from the skewer; and a hollow tube for receiving the hollow plunger therein;

wherein the hollow plunger is longer than the hollow tube and further wherein the skewer is longer than the hollow tube.

In another preferred form of the invention, there is provided a method for forming fibrin clot, the method comprising:

placing drawn blood in a vessel;

mounting a precipitator to the vessel so that the precipitator extends into the drawn blood contained in the vessel; and agitating the drawn blood so as to cause fibrin clot to form.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 10-12 show how suction may be used to draw fibrin clot into the coring tube;

FIG. 20 is a schematic view showing a kit for harvesting and dispensing fibrin clot;

DETAILED DESCRIPTION OF THE PREFERRED EMBODIMENTS

Coring Tube System

In one preferred embodiment of the present invention, there is provided a novel system for harvesting and dispensing a fibrin clot, wherein the novel system comprises (i) means to draw blood; (ii) means to extract fibrin from the blood so as to form a fibrin clot; (iii) means for molding, cutting and shaping the fibrin clot into a desired configuration; and (iv) means for reliably and controllably dispensing the fibrin clot at a selected location in the body, whereby to facilitate healing.

Figure 1:
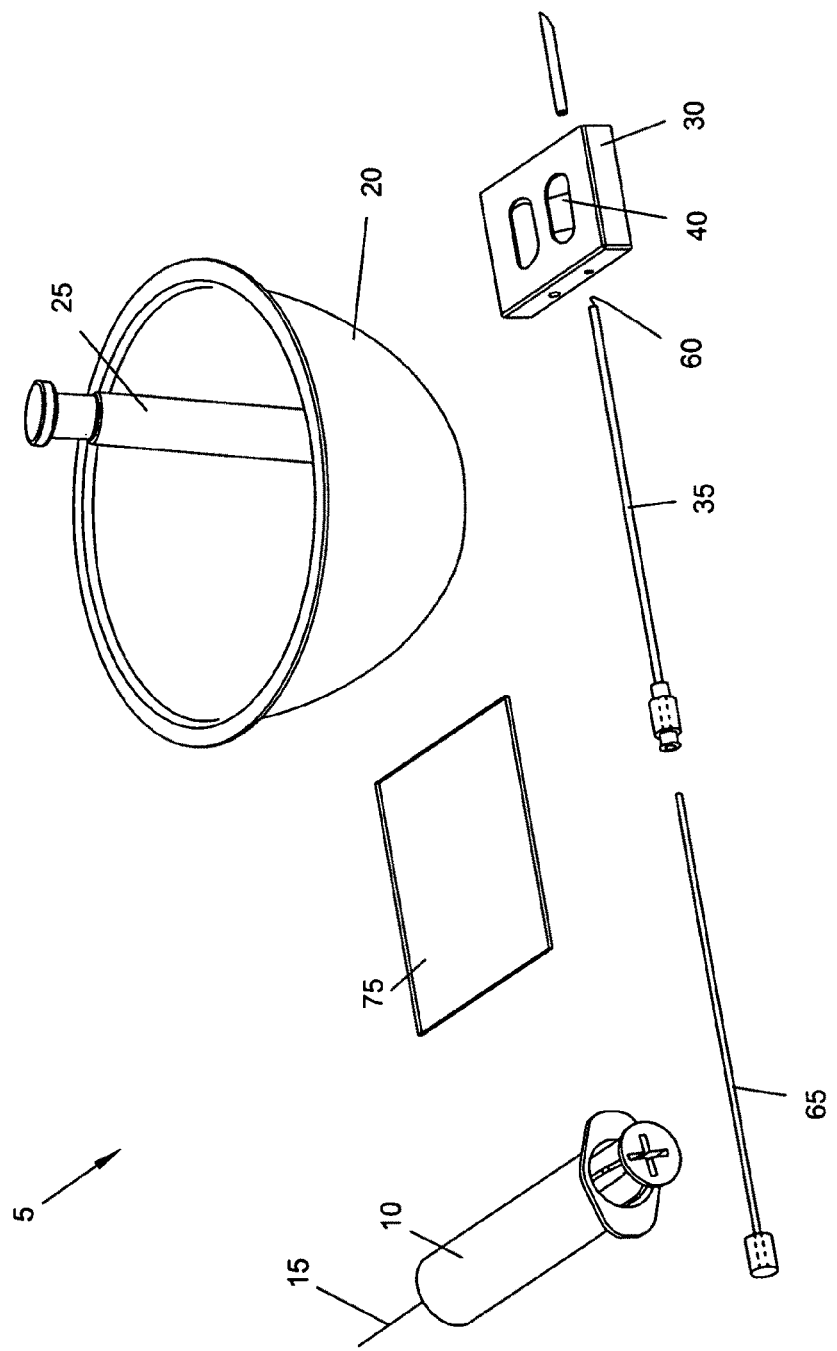
FIG. 1 is a schematic view showing a system for harvesting and dispensing a fibrin clot.

More particularly, and looking now at FIG. 1, there is shown a novel system 5 for harvesting and dispensing a fibrin clot.

Novel system 5 comprises means to draw blood, preferably in the form of a conventional blood-drawing syringe 10 including a conventional blood-drawing needle 15. If desired, the blood can be drawn from the patient who is to receive the fibrin clot (in which case the fibrin clot created from that blood may be referred to as a fibrin clot) or, alternatively, the blood can be drawn from another donor (in which case the fibrin clot created from that blood may be referred to as an exogenous fibrin clot).

Novel system 5 also comprises means to extract fibrin from the blood so as to form a fibrin clot, preferably in the form of a bowl or vessel 20 for holding the drawn blood, and a frosted glass rod 25 for stirring (i.e., agitating) the drawn blood held in bowl 20 for a period of time until a fibrin clot forms. Thus it will be seen that frosted glass rod 25 generally acts as a precipitator for the fibrin clot. If desired, frosted glass rod 25 can be replaced by another implement which is configured to precipitate fibrin clot, e.g., varied glass shapes, a metal member with a highly disrupted surface (such as a scratched surface, a holed surface, a screened surface, etc.).

Novel system 5 also comprises means for molding, cutting and shaping the fibrin clot into a desired configuration, preferably in the form of a clot preparation block 30 for receiving and holding the fibrin clot and a coring tube 35 for excising, storing, and injecting a plug or morsels of cored fibrin clot.

Figure 2:
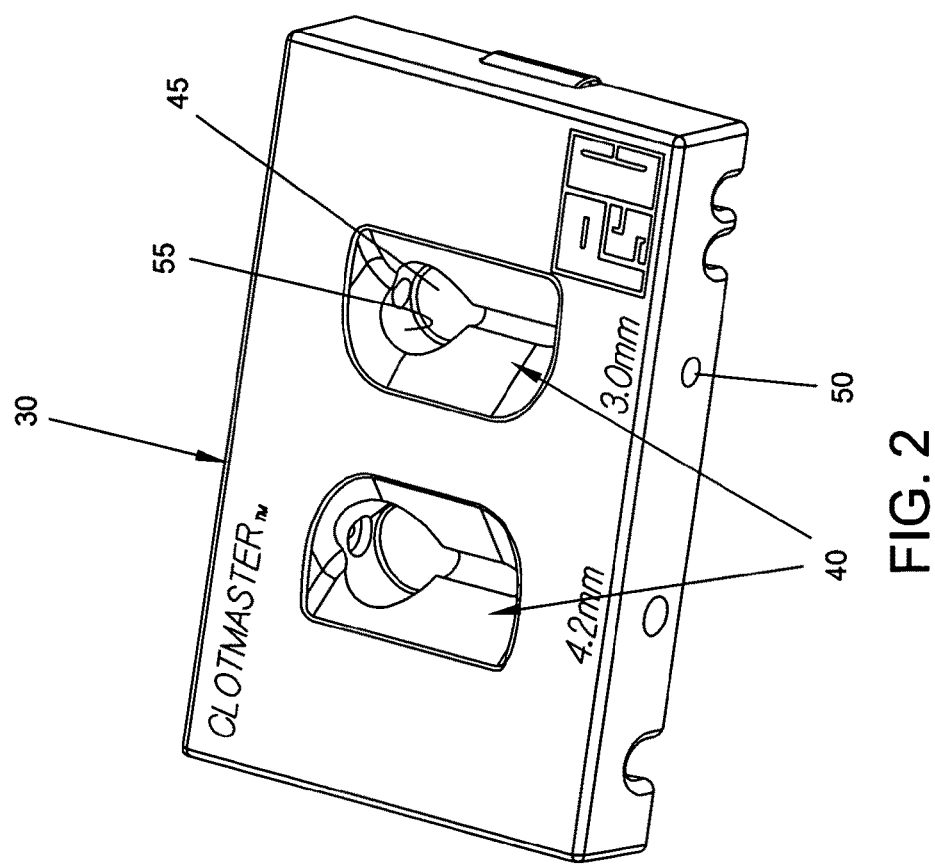
FIG. 2 is a schematic view showing further details of the clot preparation block of the system shown in FIG. 1.

More particularly, and as seen in FIGS. 1 and 2, clot preparation block 30 preferably comprises at least one chamber 40 generally in the form of a funneled hopper and having a coring well 45 disposed at its bottom end. A bore 50 extends through clot preparation block 30 and communicates with chamber 40. A stop face 55 is disposed in chamber 40, diametrically opposed to bore 50. Coring tube 35 preferably comprises a relatively sharp distal rim 60. On account of the foregoing construction, and as will hereinafter be discussed in further detail, when a fibrin clot is disposed in chamber 40 of clot preparation block 30, and coring tube 35 is thereafter advanced through bore 50, across chamber 40, and against stop face 55, coring tube 35 will core out a plug of the fibrin clot and store the cored fibrin clot within the lumen of coring tube 35. If desired, coring tube 35 may be passed through chamber 40 just once so as to core out a plug of the fibrin clot and store that plug within the interior of coring tube 35. Alternatively, coring tube 35 may be passed through chamber 40 multiple times, preferably with the fibrin clot being repacked within chamber 40 between passes of the coring tube, so as to core out a plurality of cored fibrin clots and store those plugs within coring tube 35. Alternatively, coring tube 35 may be pressed freehand downward onto the clot held in chamber 40 using the flat bottom of the chamber 40 as a backstop.

Novel system 5 also comprises means for reliably and controllably dispensing the cored fibrin clot at a selected location in the body, preferably in the form of a plunger 65 which is passed through the lumen of coring tube 35 so as to expel the cored fibrin clot into the body. The length of plunger 65 is preferably slightly longer than the length of coring tube 35, so that when the plunger is completely inserted within the coring tube, the tip of the plunger extends beyond the end of the coring tube, whereby to ensure that the cored fibrin clot is completely ejected from the coring tube and that no material sticks or clings to the end of the coring tube. Plunger 65 can be mounted in coring tube 35 either before or after the coring tube has been used to core plugs of fibrin clot from chamber 40. In one preferred form of the invention, plunger 65 is inserted into coring tube 35 after the coring tube has cored out a plug of the fibrin clot and while the coring tube is still in engagement with stop face 55, so as to cause plunger 65 to closely "pack" the cored out morsels of fibrin clot within the coring tube. Furthermore, in one preferred form of the invention, plunger 65 includes graduated markings on its shaft so that the amount of fibrin clot stored in coring tube 35 and/or expelled from coring tube 35 can be measured.

System 5 may be used in the following manner to harvest a fibrin clot and deposit that fibrin clot into a wound site:

1. Blood is drawn from the patient using syringe 10 and needle 15 (FIG. 1).

Figure 3:
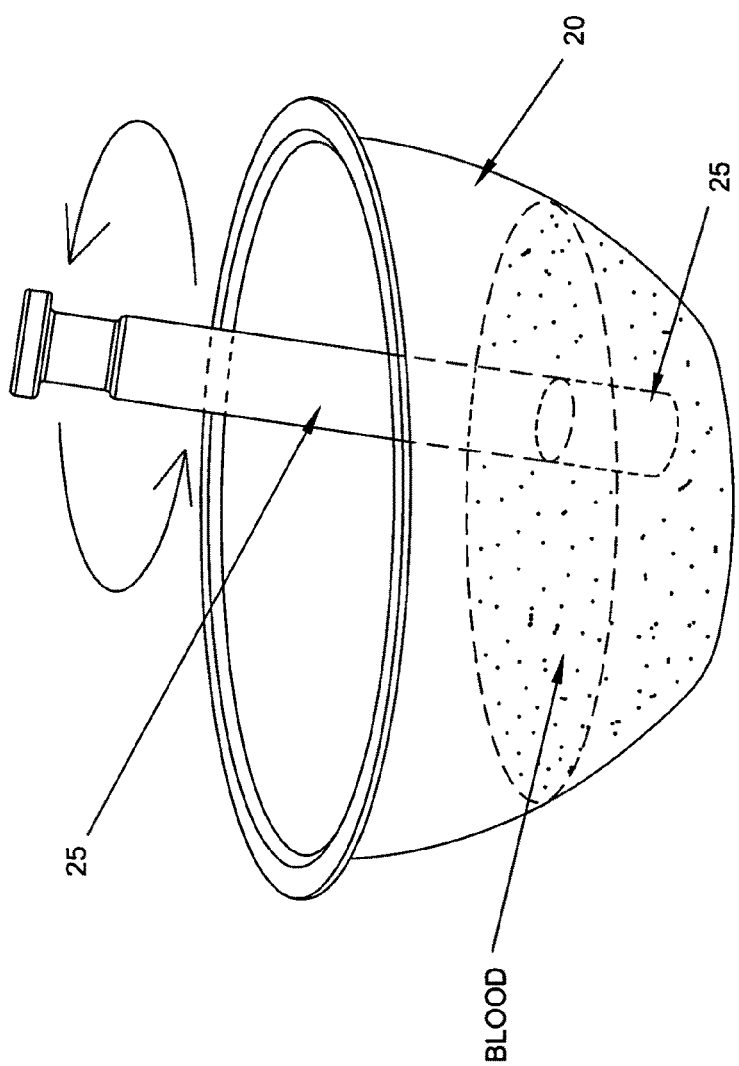
FIG. 3 is a schematic view showing drawn blood being stirred in a vessel so as to precipitate fibrin clot.

2. The blood is transferred from syringe 10 to bowl 20 (FIG. 3).

Figure 4:
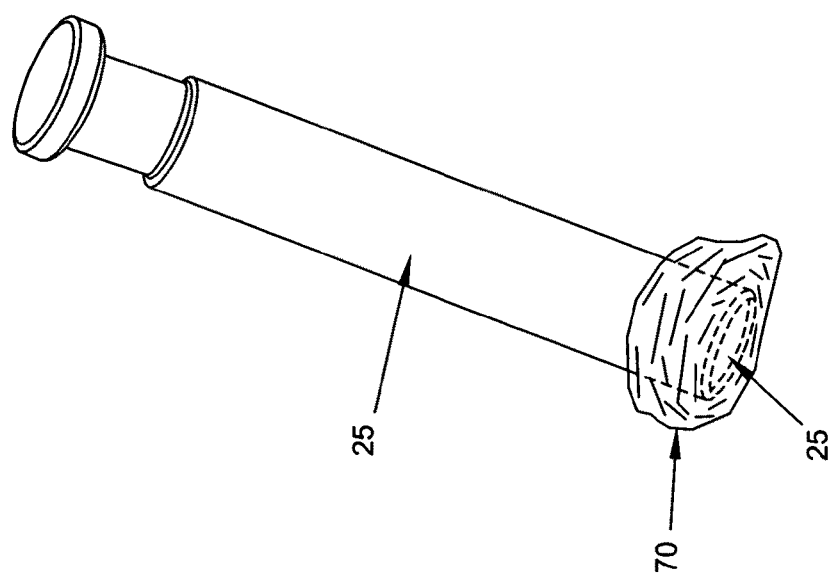
FIG. 4 is a schematic view showing fibrin clot precipitated on a frosted glass rod.

3. Once the blood is in bowl 20, the blood is stirred with frosted glass rod 25 until fibrin clot 70 precipitates on frosted glass rod 25 (FIG. 4).

4. The fibrin clot 70 is removed from frosted glass rod 25, e.g., with gauze 75 (FIG. 1), preferably blotting off excess liquid.

Figure 5:
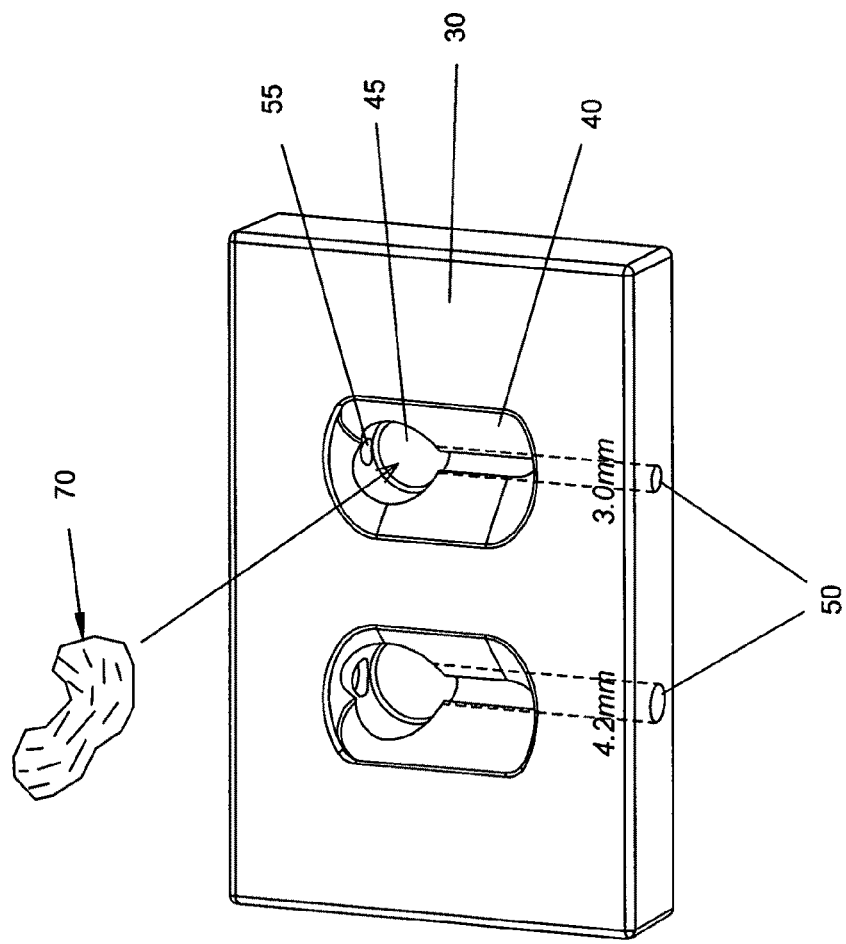
FIG. 5 is a schematic view showing a fibrin clot being deposited in the clot preparation block.

5. The fibrin clot 70 is placed into chamber 40 of clot preparation block 30 (FIG. 5).

6. The fibrin blood clot 70 is forced deep into chamber 40 and into coring well 45 at the base of the chamber, e.g., using gauze 75.

Figure 6:
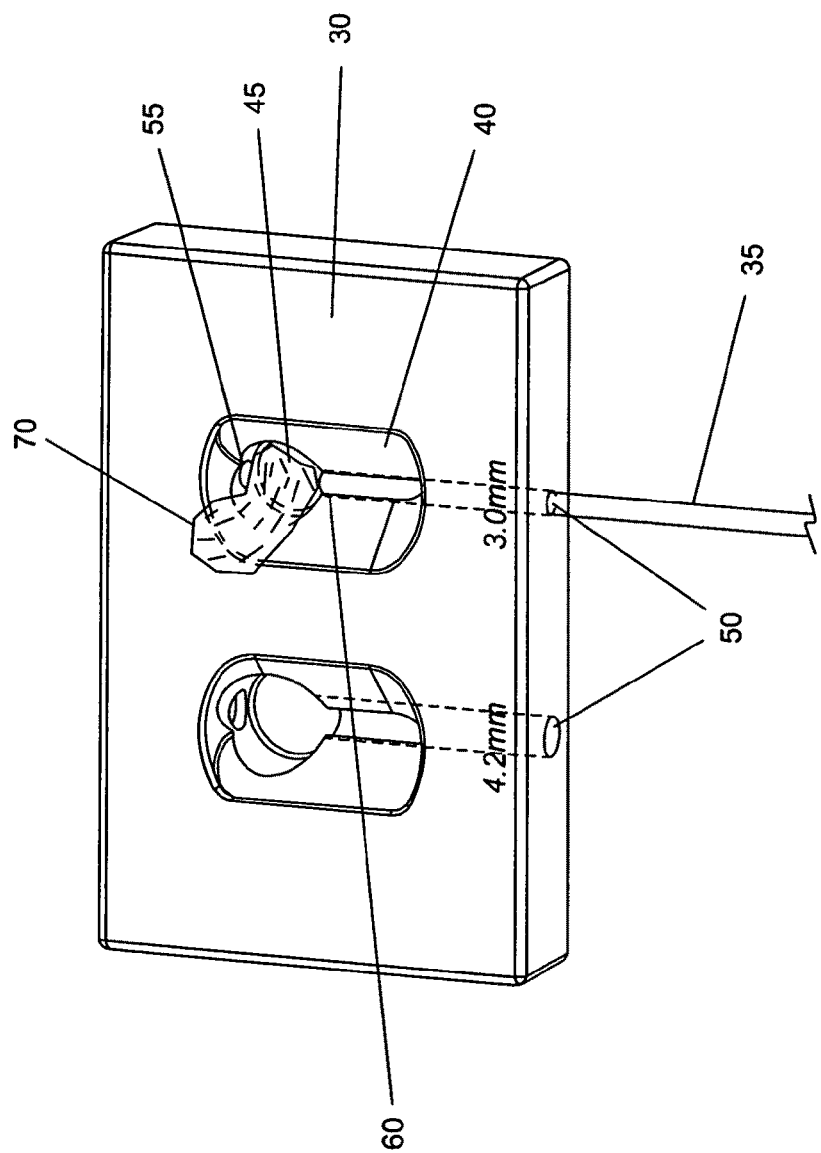
FIG. 6 is a schematic view showing a coring tube being advanced into engagement with the fibrin clot.
Figure 7:
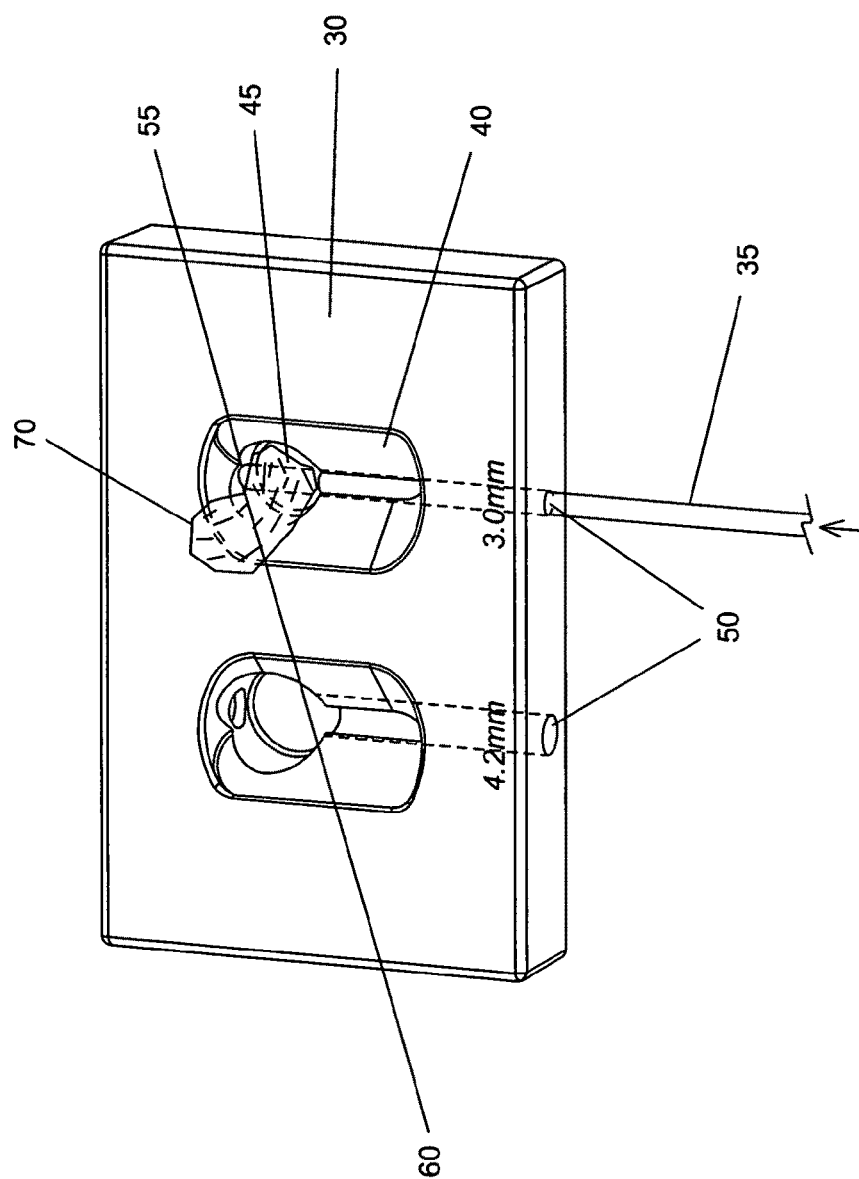
FIG. 7 is a schematic view showing the coring tube coring the fibrin clot while the fibrin clot is disposed in the clot preparation block.

7. Coring tube 35 is advanced through bore 50 of clot preparation block 30 until the distal end of coring tube 35 passes through coring well 45, coring the fibrin clot 70 as it goes (FIGS. 6 and 7). Forward movement of coring tube 35 preferably continues until the distal end of coring tube 35 engages stop face 55 of clot preparation block 30.

Figure 8:
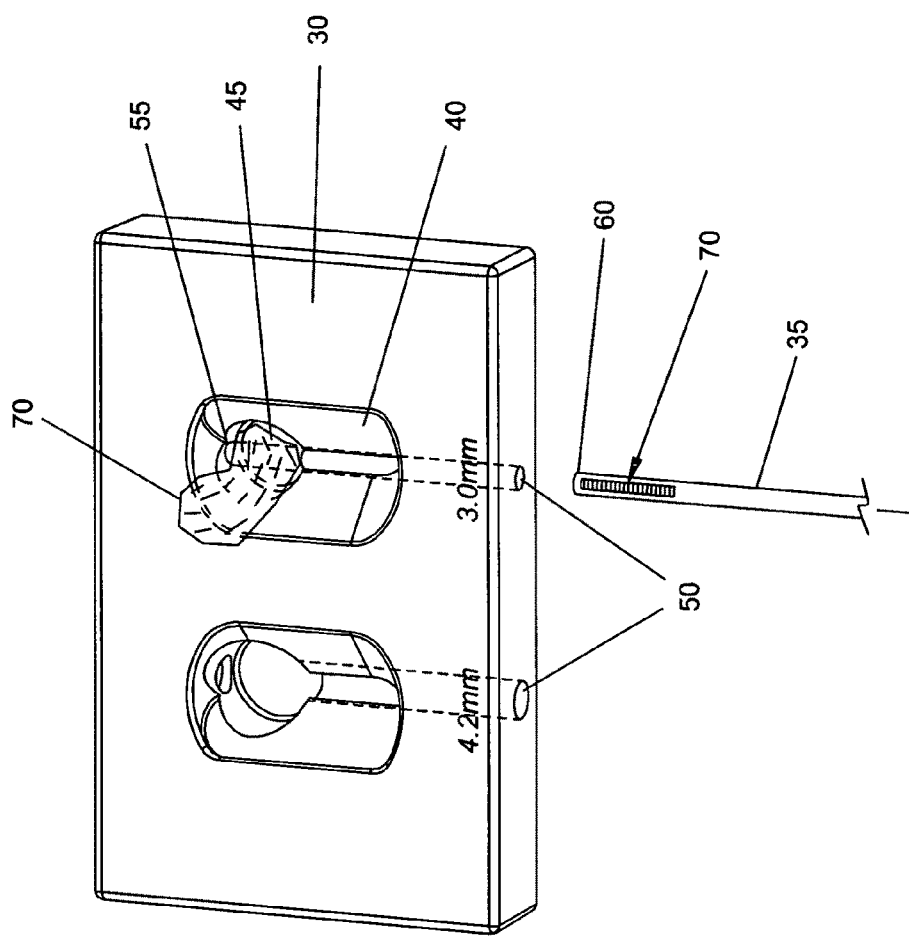
FIG. 8 is a schematic view showing the coring tube retracting from the clot preparation block, carrying cored fibrin clot with it.
Figure 9:
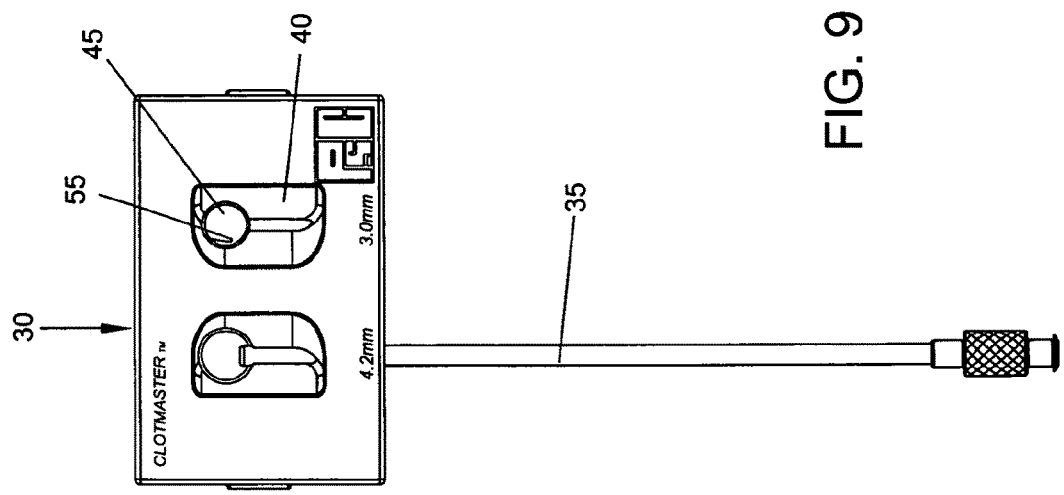
FIG. 9 is a schematic view showing a coring tube disposed in a clot preparation block.

8. With coring tube 35 engaging stop face 55, the coring tube is twisted back and forth so as to further core the fibrin clot, whereby to store a plug of fibrin clot within the interior of coring tube 35. If desired, plunger 65 can have been inserted in the lumen of coring tube 35 as the coring tube cores the fibrin clot, in which case the plunger will back out of the coring tube as the coring tube fills with the plug of fibrin clot, thereby providing a visual indication of the amount of fibrin clot stored in coring tube 35. Coring tube 35 is then withdrawn from clot preparation block 30 (FIG. 8).

9. If it is desired to increase the amount of fibrin clot stored in coring tube 35, the fibrin clot in chamber 40 can be pressed back down into coring well 45, and then Steps 7 and 8 above repeated so as to increase the amount of fibrin clot stored in coring tube 35.

10. When the desired amount of fibrin clot 70 has been captured in the lumen of coring tube 35, the coring tube and its associated plunger 65 are inserted into the body adjacent to the wound site where the fibrin clot is to be deployed.

11. The distal tip of coring tube 35 is advanced through the body until it is disposed adjacent to the site where the fibrin clot is to be deployed (which may include passing the distal tip of the coring tube through intervening tissue), and then plunger 65 is advanced distally so as to expel the fibrin clot into the tissue.

Significantly, since the fibrin clot comprises an elongated cylindrical structure within the coring tube, ejection of the fibrin clot from the coring tube can involve delivery of a plurality of separate "beads" of fibrin clot at separate locations at the wound site, or the delivery of an elongated "continuous bead" of fibrin clot material at the wound site.

Vacuum System

In the foregoing description, mechanical engagement of coring tube 35 with stop face 55 is used to core a segment of the fibrin clot into the interior of the coring tube. However, other arrangements are also possible.

For one thing, suction can be applied to the proximal end of coring tube 35 so as to draw a segment of the fibrin clot into the interior of the tube, with the cored segment of the fibrin clot separating from the remainder of the fibrin clot mass as the suction overcomes the integrity of the fibrin clot mass. See FIGS. 9-12.

Furthermore, in the foregoing description, plunger 65 is used to expel the cored fibrin clot from the coring tube. However, if desired, pressure can be applied to the proximal end of the coring tube so as to expel the cored fibrin clot from the interior of the coring tube.

Suture System

It is also possible to mount the cored fibrin clot onto a suture so that the suture can be used to manipulate the cored fibrin clot, whereby to facilitate its placement at the surgical site. Among other things, the cored fibrin clot can be run down the suture so as to facilitate deployment of the cored fibrin clot. This feature can be extremely useful in situations where a suture anchor may be deployed in bone and the suture emanating from the suture anchor used to "tie down" soft tissue (e.g., a ligament) to the bone. In such a situation, mounting the cored fibrin clot onto the suture provides a fast and simple way to ensure that the fibrin clot is deployed at the location where the suture emanates from the bone, i.e., at the precise location where the soft tissue is to be reattached to the bone.

Figure 13:
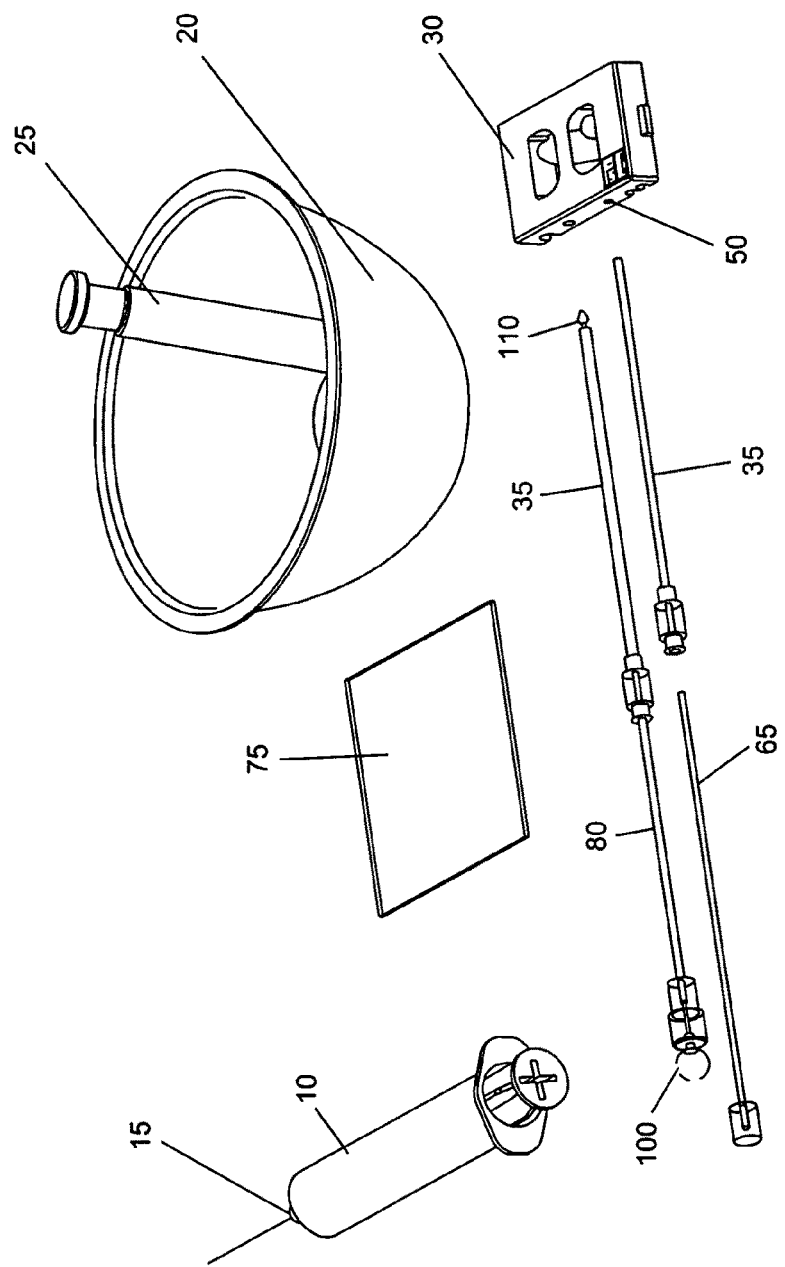
FIG. 13 is a schematic view showing an alternative system for harvesting and dispensing a fibrin clot.
Figure 14:
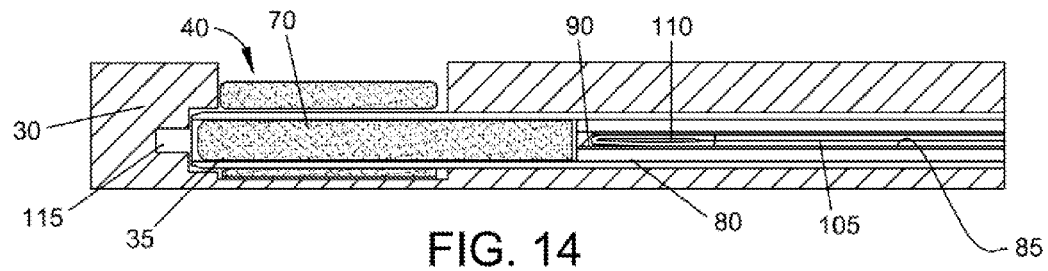
FIGS. 14-19 are schematic views showing how the system of FIG. 13 may be used to harvest and dispense fibrin clot.
Figure 15:
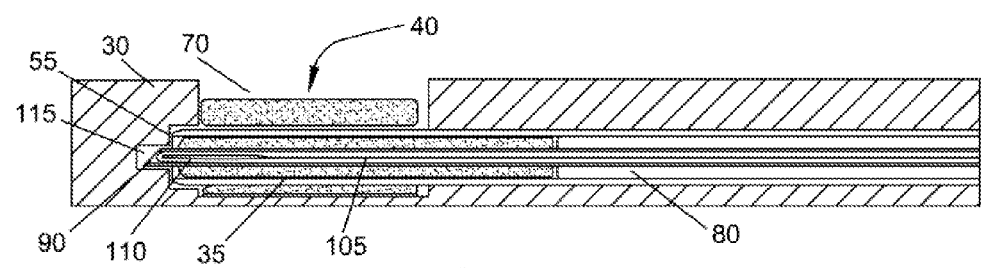
Figure 16:
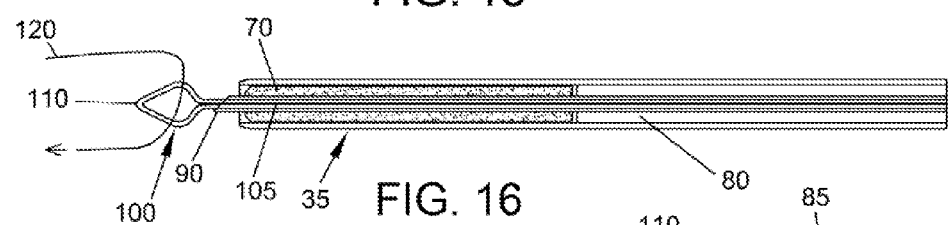
Figure 17:
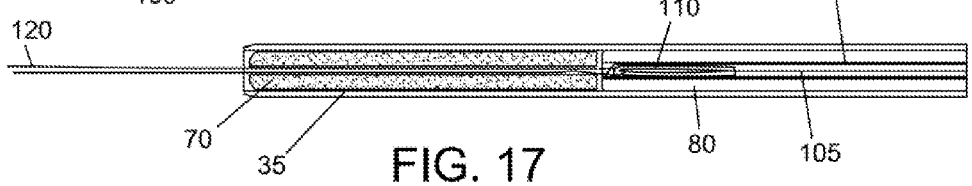
Figure 18:
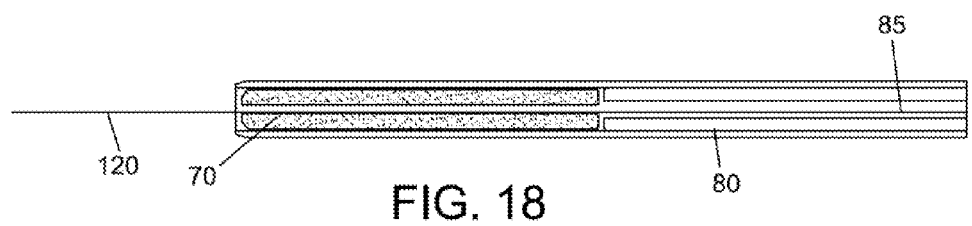
Figure 19:
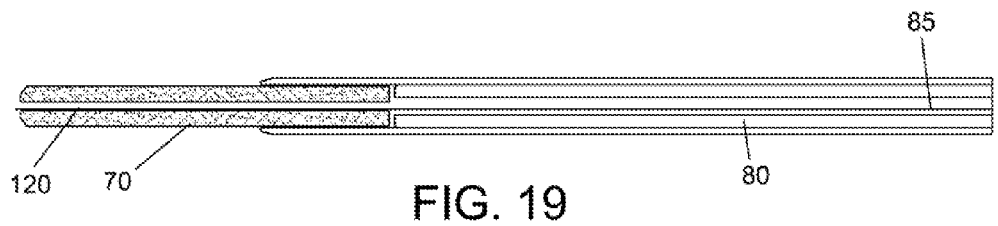

More particularly, in this alternative form of the invention, and looking now at FIG. 13, there is provided the aforementioned coring tube 35, a modified plunger 80 having a lumen 85 (FIG. 14) extending therethrough, a sharp passer tube 90, and a suture retriever 100 comprising a shaft 105 having a suture pickup loop 110 at its distal end (FIG. 16). In this form of the invention, and looking now at FIG. 14, after fibrin clot 70 has been disposed in chamber 40 in clot preparation block 30, and after coring tube 35 has been passed through the mass of the fibrin clot 70, sharp passer tube 90 is passed through plunger 80 and coring tube 35 until the distal end of the sharp passer tube passes through fibrin clot 70 and enters a recess 115 formed in stop face 55. As this occurs, fibrin clot 70 is prevented from extruding from coring tube 35 by stop face 55 (FIG. 15). Then coring tube 35 is retracted from clot preparation block 30, with the distal tip of sharp passer tube 90 standing proud of the end of coring tube 35 and fibrin clot 70. Next, suture retriever 100 is passed down sharp passer tube 90 so that suture pickup loop 110 extends out the distal end of sharp passer tube 90 (FIG. 16). Then suture 120 is loaded into suture pickup loop 110, and suture retriever 100 is retracted back through sharp passer tube 90 so as to pull suture 120 through fibrin clot 70 (FIG. 17). Thereafter, when the cored fibrin clot is to be deployed in the body, suture 120 is held taut outside of the body (FIG. 18), plunger 80 is moved distally so as to expel fibrin clot 70 from coring tube 35 (FIG. 19). As noted above, suture 120 may be the suture emanating from a bone anchor deployed in bone, in which case mounting the cored fibrin clot onto the suture provides a fast and simple way to ensure that the fibrin clot is deployed at the location where the suture emanates from the bone, i.e., at the precise location where the soft tissue is to be reattached to the bone. Alternatively, suture 120 may be suture from another source.

Alternatively, if desired, suture 120 can be omitted, and sharp passer tube 90 can be used as a sort of retractable skewer to hold the fibrin clot impaled thereon, and to subsequently help manipulate the fibrin clot after it is ejected from the coring tube. The skewer (i.e., sharp passer tube 90) can be retracted against plunger 80 to help strip impaled fibrin clots from the skewer.

Thus it will be seen that the present invention provides means to safely apply suture to fibrin clot 70 without the risk of needle stick injuries, by providing a clot preparation block which includes a chamber for receiving the fibrin clot and a protective backstop for cutting clot morsels with the sharp coring tube and for protected needle passing for drawing the suture through the fibrin clot. Alternately, suction can be applied to the coring tube so as to load the coring tube with liquid or flowable gel clot from the chamber. The coring tube and plunger provide means to contain and control the clot-suture construct while introducing the clot-suture construct into the body, and means to release the clot from the coring tube, and means to run the fibrin clot down the suture to the repair site so that the clot can closely approximate the defect site. Furthermore, the suture can be used to secure the fibrin clot to adjacent tissue at the repair site.

The invention also comprises means to eject fibrin clot at an angle to the longitudinal axis of the coring tube, by providing a curved tip 125 (FIG. 20) for the coring tube, or by means of a malleable central wire or shaft upon which the fibrin clot may be impaled.

The surgical method includes the steps of performing arthroscopic surgery on a knee, hip or elbow joint, or other joint, by placing a number of small incisions in the skin adjacent to the area of the joint. Viewing apparatus, which may preferably be an arthroscope, is positioned into the joint. The physician inserts a number of cutting and suctioning tools into the wound site to repair the damage seen therein. Thereafter, the coring tube of the present invention, which has been filled with a pre-determined amount of fibrin clot and has its plunger partially inserted therein, is inserted into the joint. The physician, while viewing the operation through an arthroscope, manipulates the coring tube and its plunger, preferably with one hand, so as to eject the cored fibrin clot into the wound or damaged tissue site where needed. The physician can determine the amount of fibrin clot ejected by visualizing the graduated marks located on the shaft of the plunger, or by watching the relationship between the plunger handle and the proximal end of coring tube. If suture is threaded though the fibrin clot, the physician can hold the suture taut and run the applicator assembly down the suture to the repair site. In one form of the invention, the suture threaded through the fibrin clot in the coring tube emanates from soft or hard tissue or from a suture anchor disposed at the surgical site. The physician then removes the applicator device and stitches the wound site closed to complete the operation and allow the joint to heal.

"Cookie Cutter" Construction

In yet another form of the invention, the fibrin clot gathered on the precipitator (e.g., frosted glass rod 25) is deposited on a flat surface, and then coring tube 35 is pressed down against the fibrin clot deposited on the flat surface so as to core the fibrin clot using the rim of the coring tube, in a cookie cutter sort of fashion. This action cores plugs of fibrin clot from the large flat sheet of fibrin clot, and loads those plugs into the interior of the coring tube. If desired, the fibrin clot may be dried and/or compressed prior to such coring.

In another form of the invention, a fibrin clot having an amorphous shape is deposited in a recess comprising a flat surface which acts as a "cutting board" for the distal end of the coring tube and parallel or angled sides which serve to centralize the clot mass into the path of the coring tube, thereby increasing the size of the plugs.

Shaker Precipitator

In the foregoing description, a frosted glass rod is used to stir the drawn blood in an open-topped bowl until fibrin clot is formed. However, other arrangements for forming fibrin clot from the blood are also contemplated.

Figure 21:
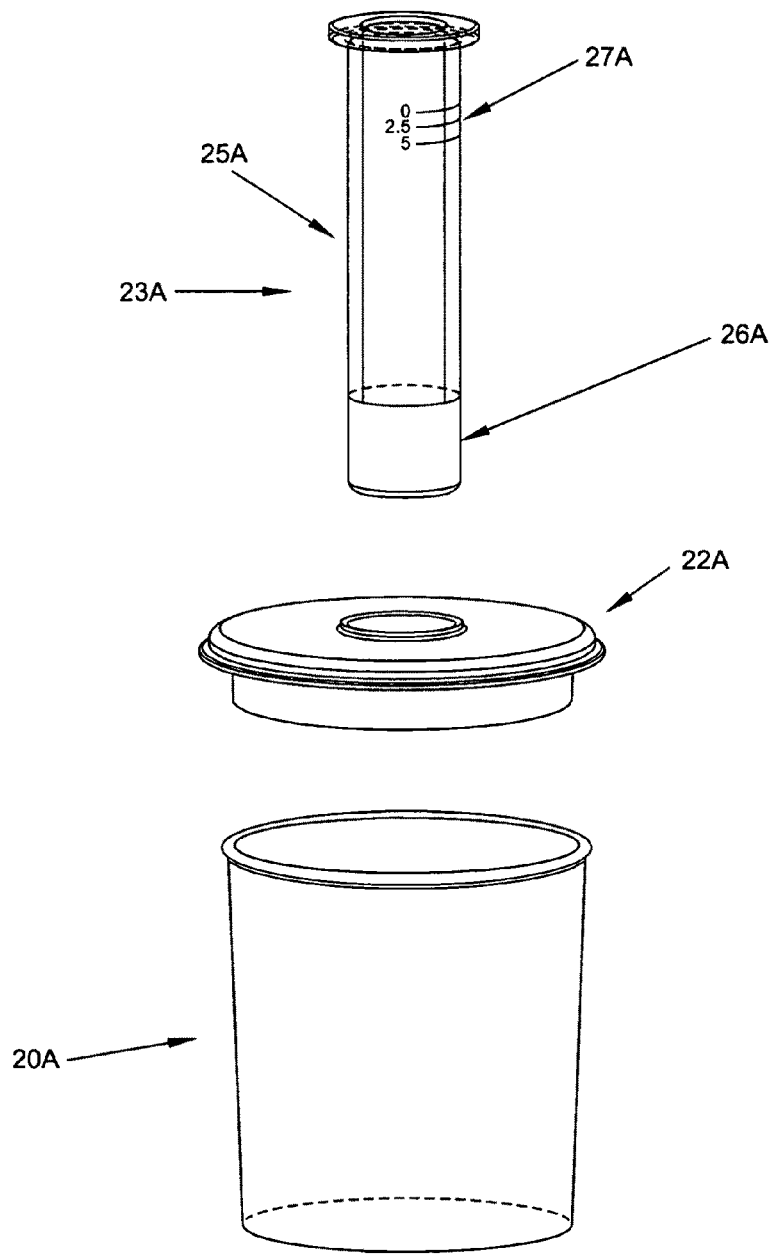
FIGS. 21 and 22 are schematic views showing alternative apparatus for forming a fibrin clot.
Figure 22:
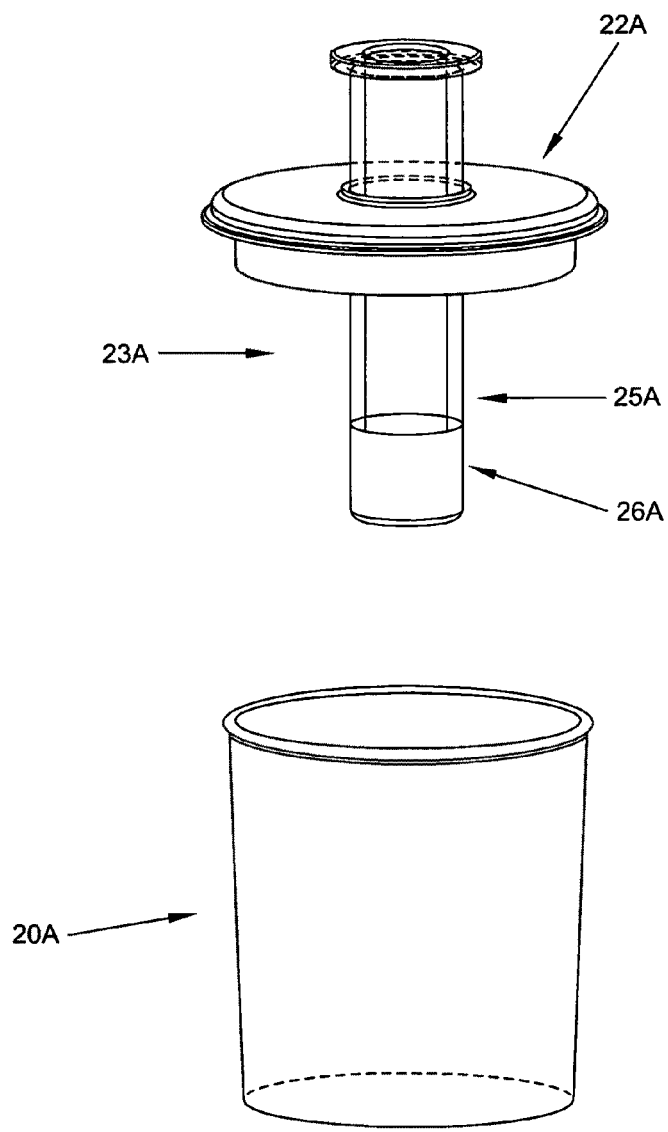

In one embodiment, and looking now at FIGS. 21 and 22, novel system 5 comprises a vessel 20A for holding the drawn blood, a lid 22A for selectively closing off vessel 20A, and a precipitator 23A for precipitating fibrin clot from the drawn blood held in vessel 20A when the drawn blood is agitated vis-à-vis precipitator 23A. In one preferred form of the invention, precipitator 23A comprises a rod 25A having an elongated shaft with a frosted glass section 26A adjacent to its distal end. Alternatively, precipitator 23A may comprise a plurality of rods, a paddle, a helical structure, a string of beads, a ball on a rod, a vane on a rod and/or any other appropriate configuration capable of precipitating fibrin clot from the drawn blood contained in vessel 20A. For purposes of the present description, the present invention will hereinafter generally be discussed in the context of rod 25A, however, it should be appreciated that the present invention is not intended to be limited to a precipitator having a rod construction.

And in one particularly preferred form of the invention, vessel 20A comprises a syringe for drawing blood, lid 22A comprises a plunger for movement along the syringe, and precipitator 23A comprises a rod along which the plunger (i.e., lid 22A) moves.

Figure 23:
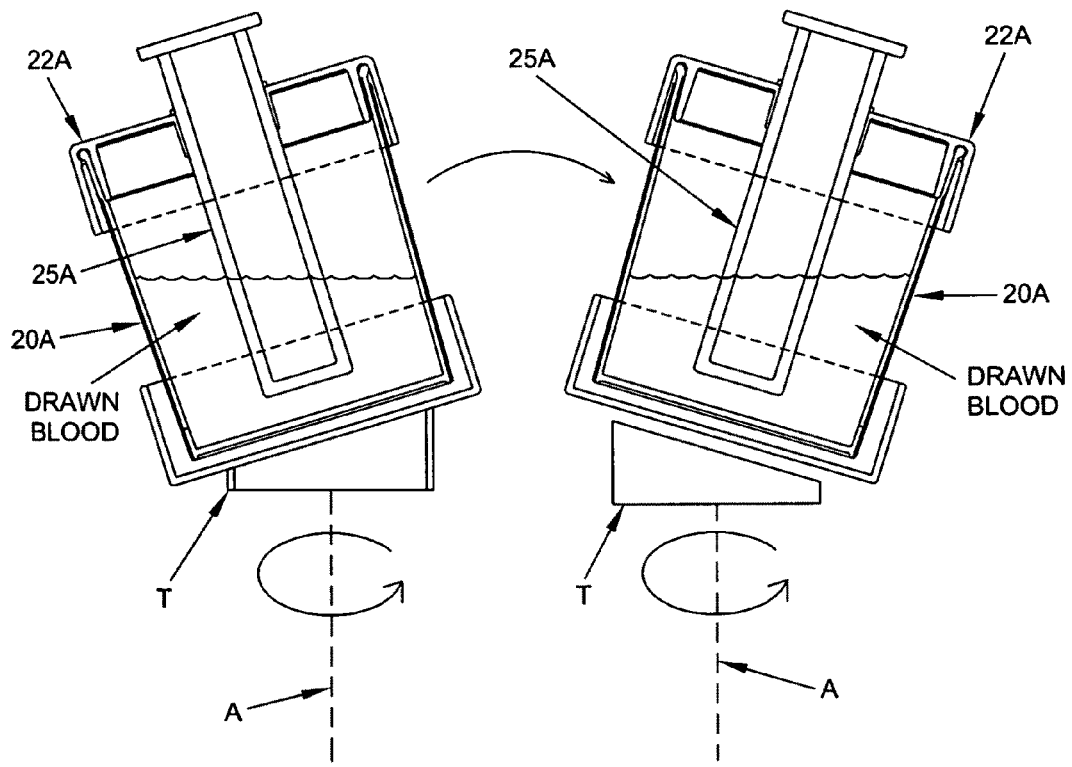
FIG. 23 is a schematic view showing how drawn blood contained within the apparatus of FIGS. 21 and 22 may be agitated about a rod by using a motorized or mechanical tilter device to move the drawn blood within a vessel.

In one preferred embodiment of the invention, vessel 20A is agitated by tilting the vessel from side to side or by rotating the vessel about a center axis, or both (e.g., in the manner shown in FIG. 23, where vessel 20A is tilted and rotated using a motorized or mechanical tilter T which rotates about a center axis A) so that the drawn blood contacts the surface of rod 25A and fibrin clot forms on rod 25A. Thus it will be seen that rod 25A acts as a focal point for the precipitation of fibrin clot when the drawn blood in vessel 20A is agitated by tilting the vessel.

Figures 24A, 24C:
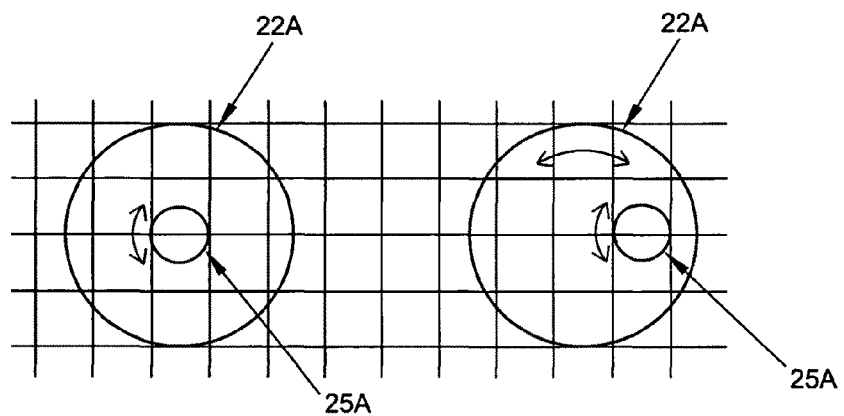
FIGS. 24A-C are schematic views showing how the position of the rod can be altered relative to the side wall of the vessel, either for the purpose of agitating the drawn blood within the vessel or for inducing different fluid flow behaviors (and hence varied clot formation) within the vessel while the vessel is externally agitated, or both.
Figure 24B:
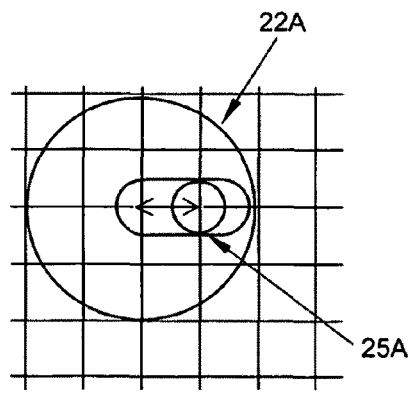

In another preferred embodiment of the present invention, the position of the rod can be altered relative to the side wall of the vessel, either for the purpose of agitating the drawn blood within the vessel or for inducing different fluid flow behaviors (and hence varied clot formation) with the vessel while the vessel is externally agitated, or both. Thus, for example, rod 25A may be rotatable relative to vessel 20A and lid 22A (FIG. 24A); and/or rod 25A may be radially movable relative to lid 22A (FIG. 24B); and/or rod 25A may be rotatable or fixed relative to lid 22A, and lid 22A may be rotatable relative to vessel 20A (FIG. 24C), etc. Significantly, by being able to move the position of rod 25A relative to vessel 20A, and particularly when the vessel is being externally agitated so as to induce blood flow within the vessel, varied and optimized fluid flow can be induced so as to cause fibrin clot to aggregate on rod 25A and/or vessel walls with desired shapes and/or consistencies. Significantly, when rod 25A is spun on its axis while in close proximity to the side wall of vessel 20A, fibrin clot of uniform thickness can be produced.

If desired, rod 25A may comprise line markings 27A (FIG. 21) along its shaft so as to indicate to the user the distance which rod 25A extends into the vessel. Alternatively, or in addition, vessel 20A can be formed with a transparent side wall so that the user can observe the distance that rod 25A extends into the vessel.

Significantly, it has been discovered that, by regulating the distance which rod 25A extends into the vessel—and, more specifically, by regulating the disposition of the distal end of rod 25A vis-à-vis the bottom surface of vessel 20A—a fibrin clot can be produced which is more uniform than the fibrin clot which can be produced by simply stirring a frosted glass rod in an open-topped bowl. This is a significant advance in the art, since a more uniform fibrin clot can be more easily handled by the user and more precisely inserted into the body.

More particularly, it has been discovered that the characteristics (e.g., shape, consistency, etc.) of the fibrin clot can be significantly influenced by the relative position of rod 25A vis-à-vis the bottom surface, or another internal surface, of the vessel.

Figure 25:
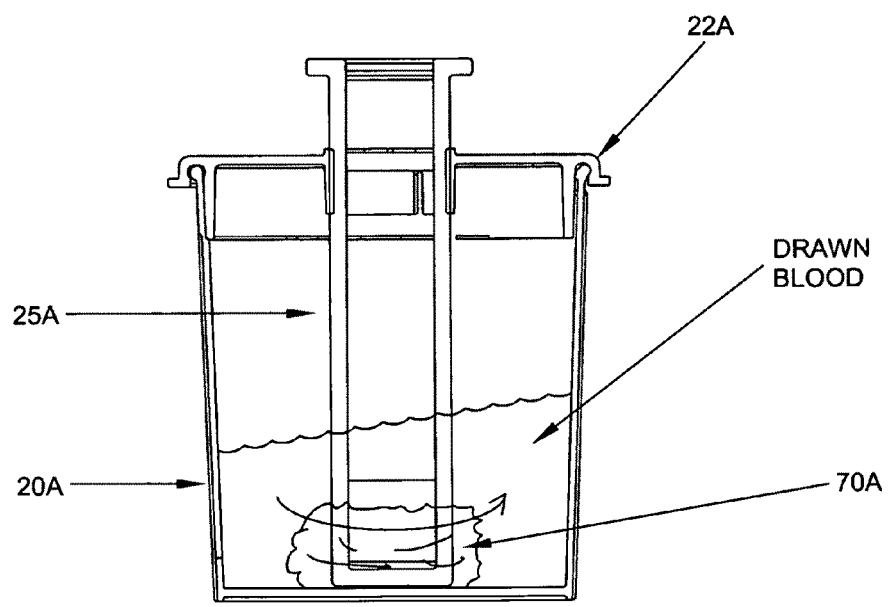
FIGS. 25-27 are schematic views showing how the disposition of a rod within a vessel (e.g., the rod and vessel of FIGS. 21 and 22) can influence the characteristics and/or configuration of a fibrin clot.

Thus, and looking now at FIG. 25, where rod 25A is positioned against the bottom surface of vessel 20A, and the vessel is thereafter gently moved so as to cause the drawn blood to swirl circumferentially around the distal end of rod 25A, the fibers of the formed fibrin clot tend to be oriented circumferentially around the rod in the direction of blood flow, and an annular (e.g., tubular, toroidal, etc.) fibrin clot 70A forms at the base of rod 25A.

Figure 26:
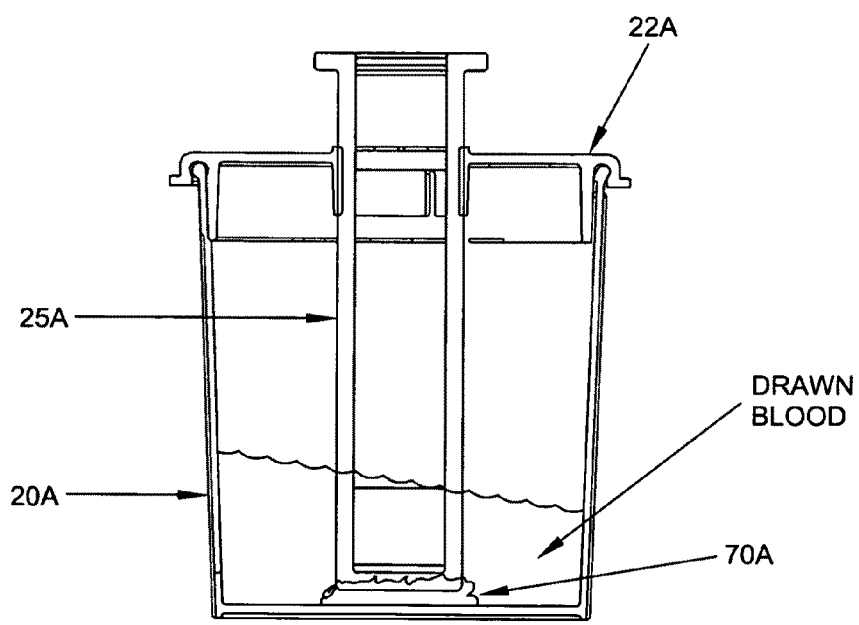

On the other hand, where rod 25A is disposed so that it is spaced somewhat from the bottom surface of vessel 20A, e.g., in the manner shown in FIG. 26, agitation of the drawn blood about rod 25A causes the fibrin clot to take the shape of a flat, discoid membrane just beneath rod 25A (i.e., in the gap between the distal end of rod 25A and the base of vessel 20A).

Figure 27:
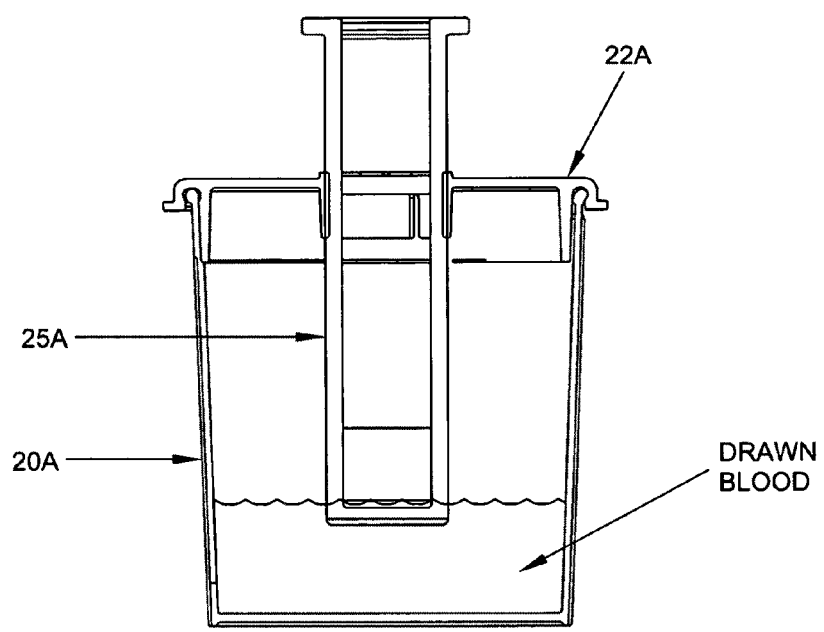

And where rod 25A is disposed so that its distal tip is located just below the surface of the drawn blood, e.g., in the manner shown in FIG. 27, and where the drawn blood is thereafter gently tilt-stirred for approximately five minutes or less and then allowed to rest (i.e., stand) for approximately another five minutes, the drawn blood typically gels into a liver-like consistency whereupon the gel can be handled without falling apart and the platelet-poor plasma can be extruded upon application, leaving an adhesive mat or infill of clot.

Preferably, rod 25A is formed out of a sintered glass rod. Rod 25 may also be formed of another material which is configured to precipitate fibrin clot, e.g., a metal member such as steel, or a non-glass material, or an open ended tube that traps air, etc.

Figure 28:
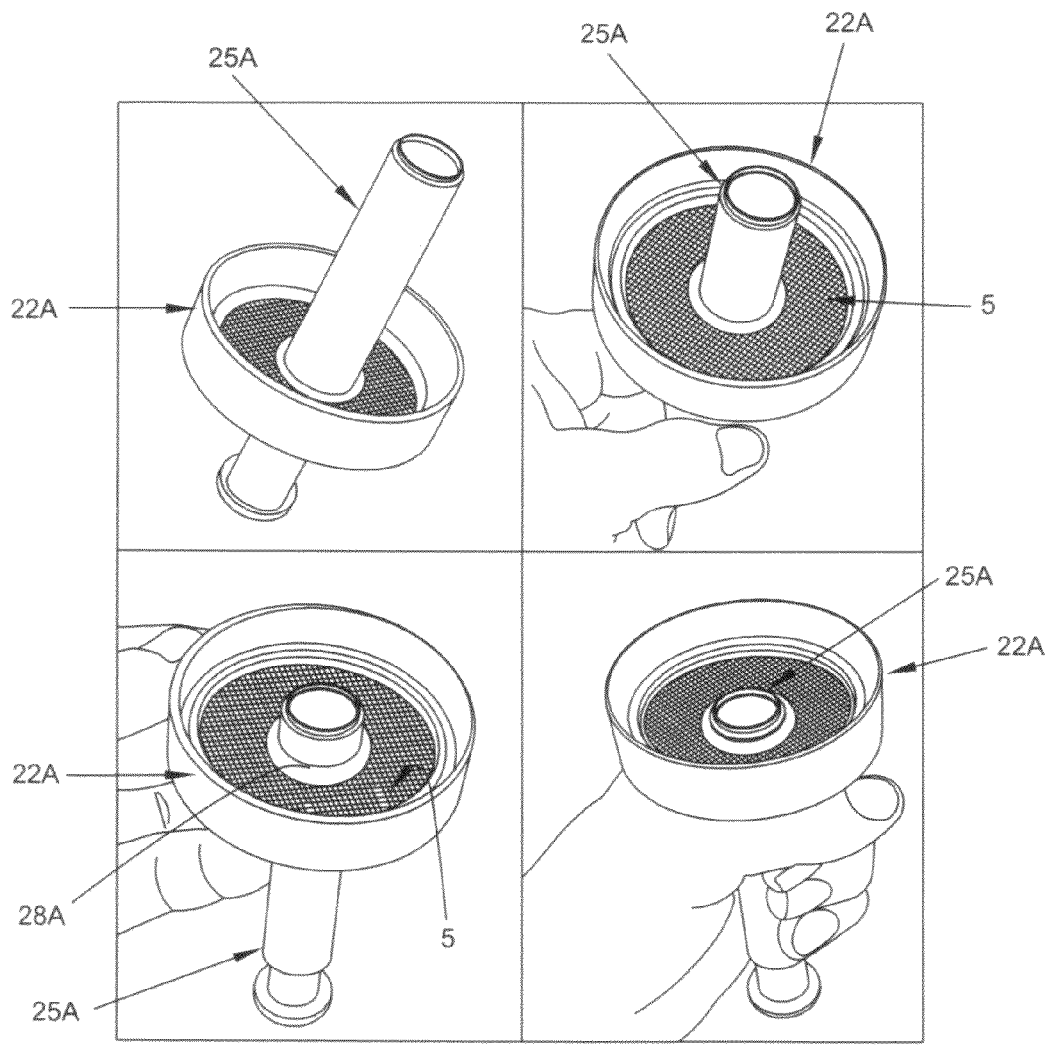
FIG. 28 is a schematic view showing how a rod can be used as a handle for a rod/lid assembly (e.g., the rod/lid assembly of FIGS. 21 and 22), and how the rod/lid assembly can be used to remove precipitated fibrin clot from the rod and hold the precipitated fibrin clot on the underside of the lid.

In another form of the invention, and looking now at FIG. 28, rod 25A can extend a substantial distance above the top of lid 22A so as to form a handle for the lid/rod assembly, thereby permitting the lid to be used upside-down on the handle (i.e., rod 25A) and serve as a container for holding the fibrin clot precipitated on rod 25A. In this respect it will be appreciated that by making rod 25A movable relative to lid 22A (e.g., in the manner shown in FIG. 28), retracting rod 25A relative to lid 22A will deposit fibrin clot clinging to rod 25A onto the underside of lid 22A. Thus, in this form of the invention, the rim 28A of lid 22A acts as a scraper on the outer surface of rod 25A to remove the fibrin clot from the rod as the rod is slid out of the lid. Preferably, the underside of lid 22A comprises a screen or absorbent material S to allow excess liquid to drain out of the fibrin clot and into the inverted lid whereby to produce of a fibrin clot of greater density.

Alternative Coring Tube

In another embodiment of the present invention, novel system 5 comprises means for molding, cutting and shaping the fibrin clot into a desired configuration, preferably in the form of clot preparation block 30 (described above) for receiving and holding the fibrin clot, and a coring tube 200 for excising and storing a plug of cored fibrin clot.

Figure 29:
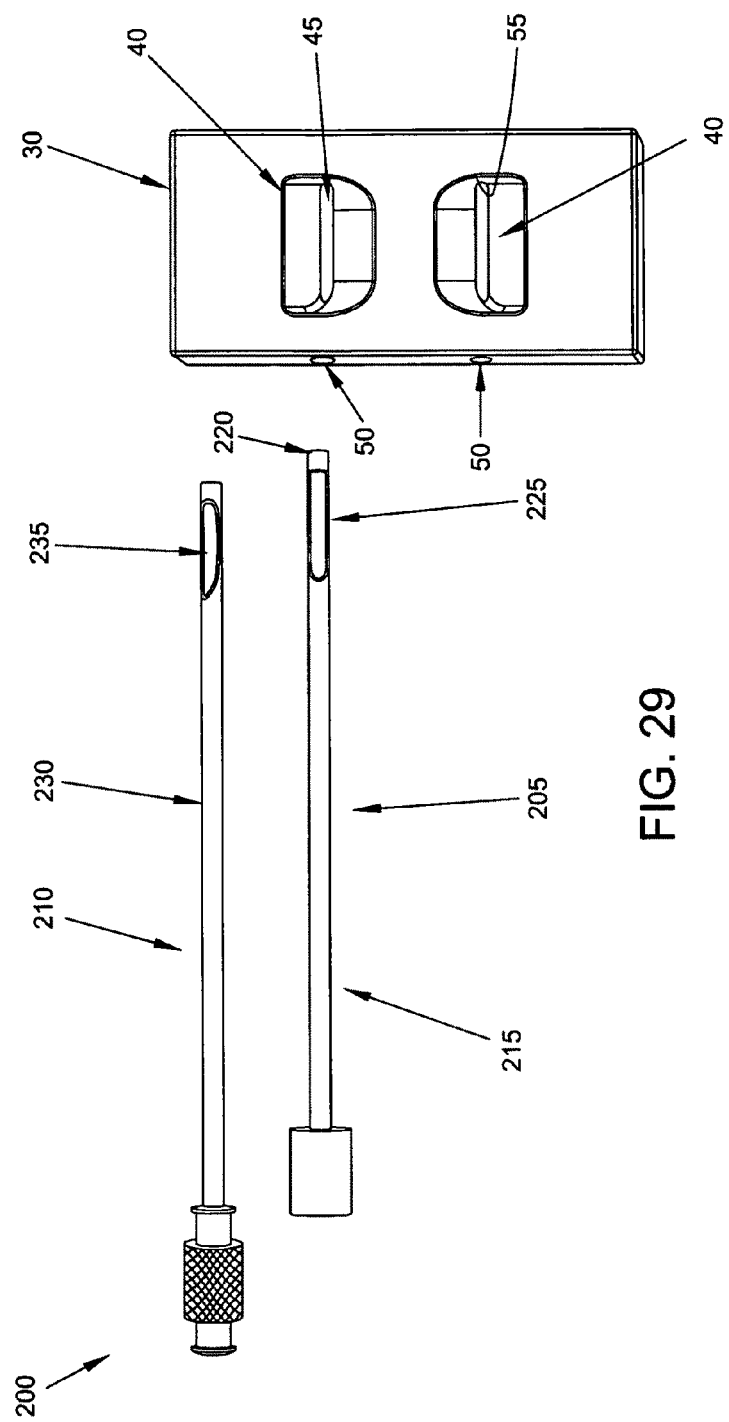
FIGS. 29 and 30 are schematic views showing an alternative form of coring tube which may be used to morselize and convey a fibrin clot.
Figure 30:
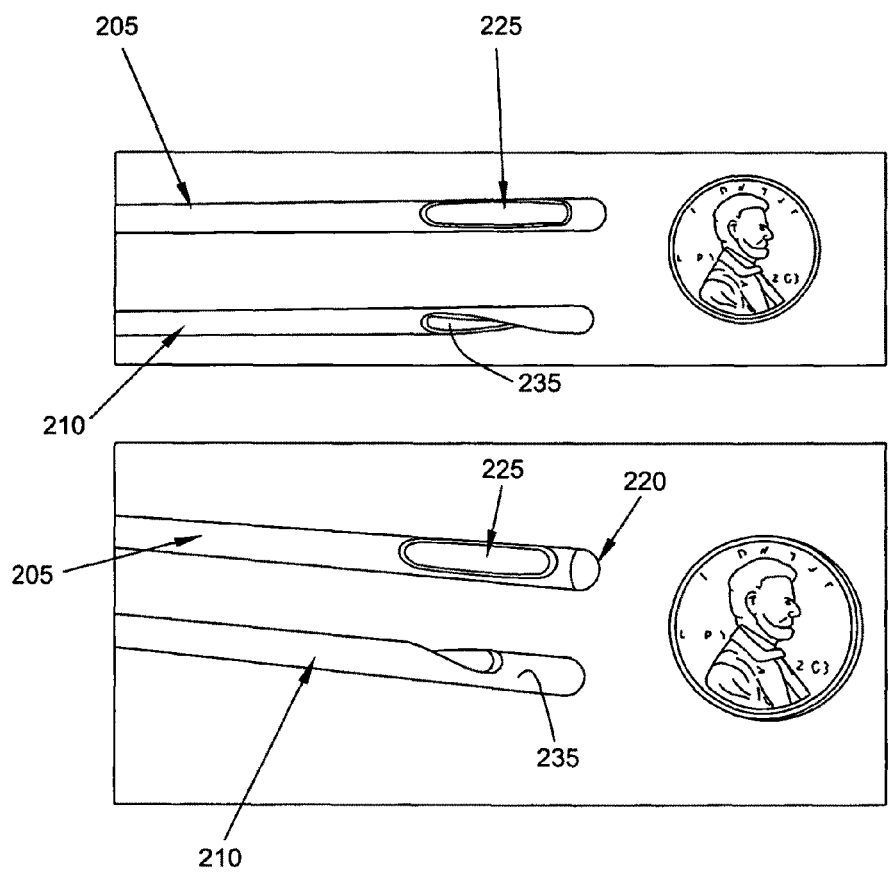

More particularly, and looking now at FIGS. 29 and 30, as discussed above, clot preparation block 30 preferably comprises at least one chamber 40 generally in the form of a funneled hopper and optionally having a coring well 45 disposed at its bottom end. Bore 50 extends through clot preparation block 30 and communicates with chamber 40. Stop face 55 is disposed in chamber 40, diametrically opposed to bore 50.

Coring tube 200 preferably comprises an outer member 205 and an inner member 210. Outer member 205 generally comprises an elongated hollow shaft 215 having a closed distal end 220 and a window 225 laterally spaced from closed distal end 220. Inner member 210 comprises an elongated shaft 230 having an open distal chamber 235 adjacent to its distal end. Preferably at least some of the edge surfaces which define open distal chamber 235 are relatively sharp. In one preferred form of the invention, inner member 210 comprises a tube. Inner member 210 is rotatably disposed within outer member 205 so that, when inner member 210 is rotated relative to outer member 205, the portions of a fibrin clot mass protruding through window 225 in outer member 205 and into open distal chamber 235 will be excised from the remainder of the fibrin clot mass and left deposited within open distal chamber 235 of inner member 210, with the excised fibrin clot having exactly the shape of open distal chamber 235. In this way, fibrin clot can be harvested from a fibrin clot mass with a uniform configuration.

On account of the foregoing construction, when a mass of fibrin clot is disposed in chamber 40 of clot preparation block 30, and coring tube 200 is thereafter advanced through bore 50, across chamber 40, and against stop face 55, with its window 225 facing the mass of fibrin clot, and inner member 210 is rotated relative to outer member 205, coring tube 200 will core out a plug of the fibrin clot mass and store that cored fibrin clot within the lumen of coring tube 200.

Figure 31:
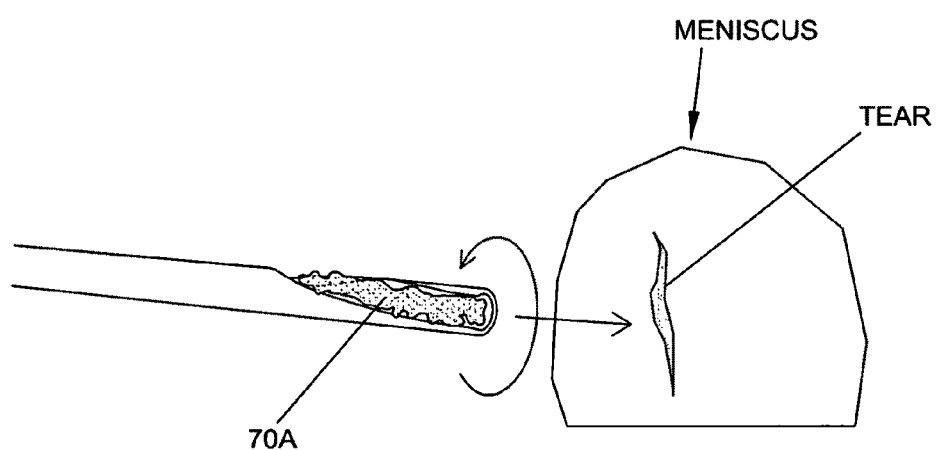
FIG. 31 is a schematic view showing the inner member of the coring tube of FIGS. 29 and 30 delivering a fibrin clot to a site within the body requiring dilation of an opening.

Significantly, inner member 210 of coring tube 200 can then be removed from outer member 205 and used as a "shoehorn" to deliver fibrin clot to a desired location in the body. By way of example but not limitation, and looking now at FIG. 31, inner member 210 can be used to deliver fibrin clot 70A to a location within the body (e.g., within the interior of a tear formed in a meniscus), whereby to facilitate accelerated healing within the body using that fibrin clot.

Figure 32:
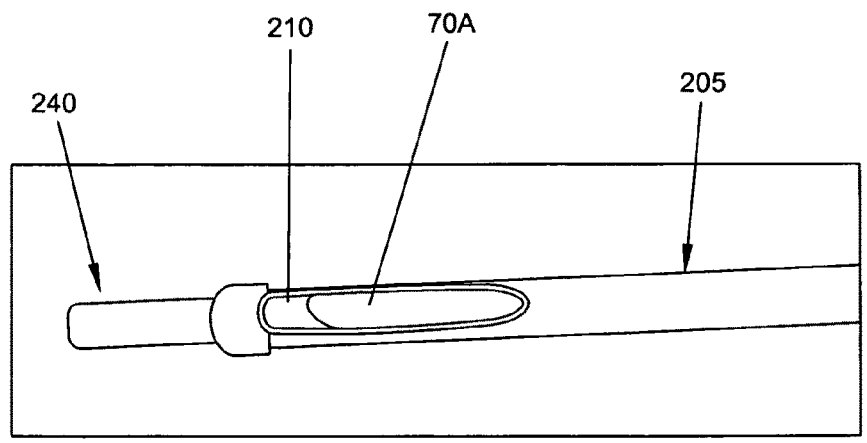
FIGS. 32 and 33 are schematic views showing an alternative form of coring tube which may be used to harvest and deliver a fibrin clot.
Figure 33:
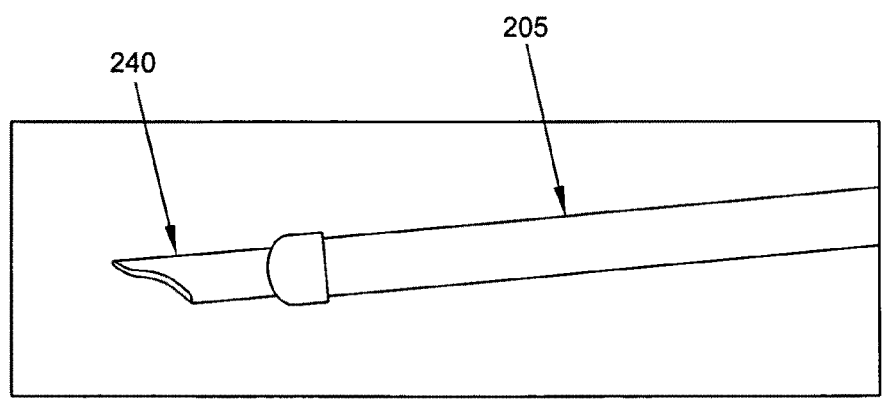
Figure 34:
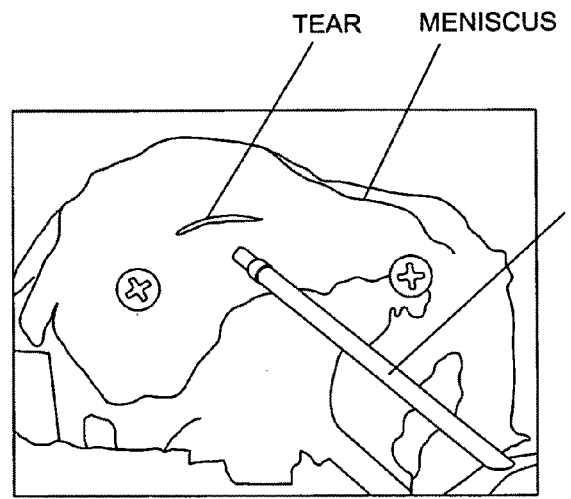
FIGS. 34-36 are schematic views showing the apparatus of FIGS. 32 and 33 delivering a fibrin clot to a site within the body.
Figure 35:
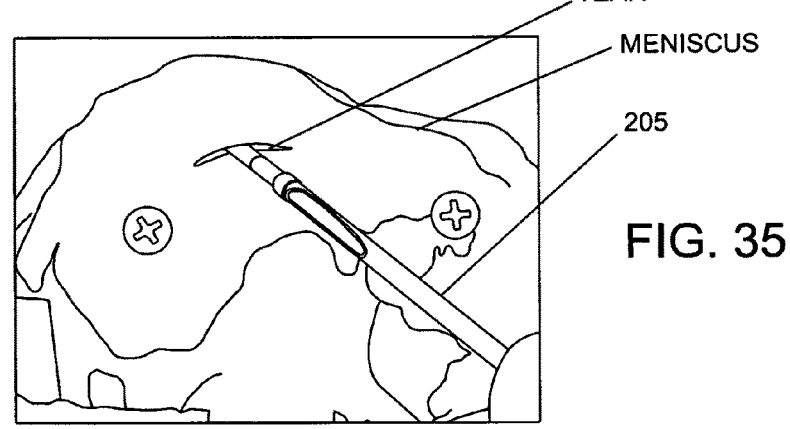
Figure 36:
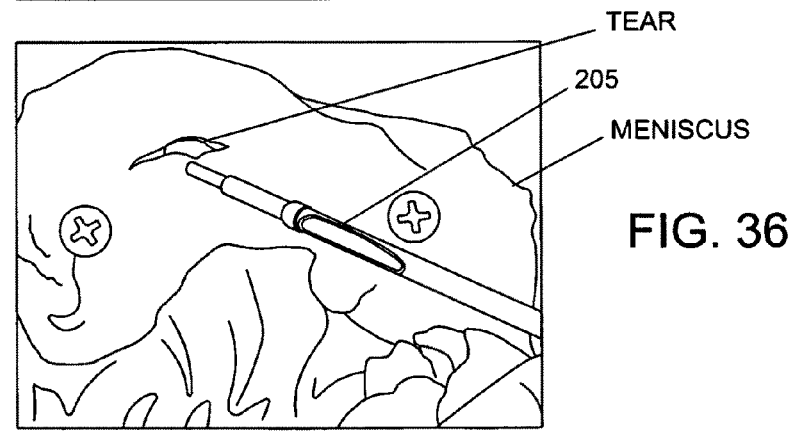

If desired, and looking now at FIGS. 32 and 33, outer member 205 may have its closed distal end 220 replaced with an atraumatic tubular extension 240. In this form of the invention, after fibrin clot has been excised from the fibrin clot mass so that it is disposed within open distal chamber 235 of inner member 210, outer member 205 and inner member 210 may be advanced as a unit into the body, the atraumatic tubular extension 240 positioned at the site where the fibrin clot is to be delivered, and then a plunger (not shown) passed down the interior of inner member 210 to eject the fibrin clot from coring tube 200. See, for example, FIGS. 34-36, which show coring tube 200 delivering fibrin clot to a meniscal tear.

Skewer-Plunger

Figure 37:
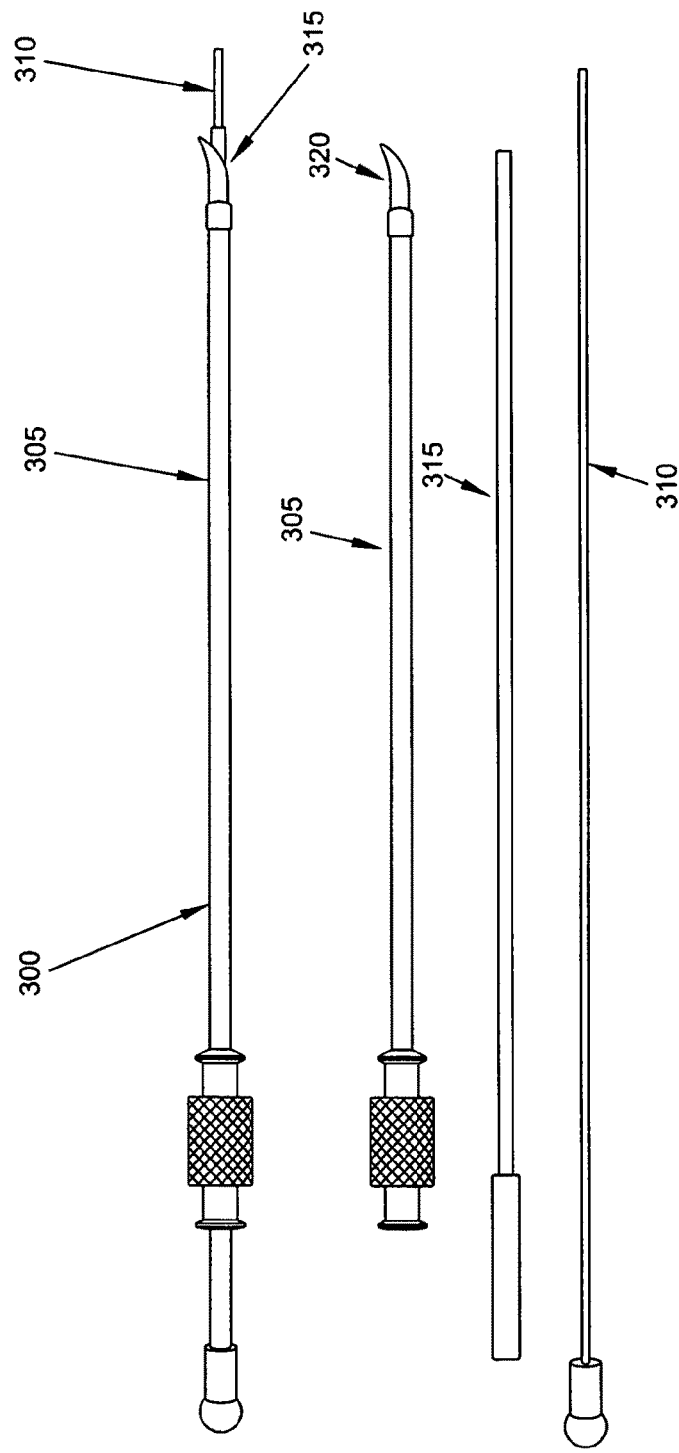
FIG. 37 is a schematic view showing additional alternative apparatus which may be used to harvest and deliver a fibrin clot.

Looking now at FIG. 37, in another form of the invention, novel system 5 comprises means for reliably and controllably dispensing the cored fibrin clot at a selected location in the body, preferably in the form of a combination skewer-plunger 300 which picks up the cored fibrin clot, stores the cored fibrin clot within the skewer-plunger and then dispenses the cored fibrin clot into the body.

Skewer-plunger 300 comprises an elongated hollow rod 305 for coring (or otherwise encompassing) a fibrin clot, a skewer 310 disposed within elongated hollow rod 305 for piercing the fibrin clot, and a hollow plunger 315 disposed within elongated hollow rod 305 and slidably disposed on skewer 310 for moving the fibrin clot off skewer 310 and into the body. In one preferred form of the invention, skewer 310 comprises a simple shaft, with or without a sharp point at its distal end; in another form of the invention, skewer 310 comprises a guidewire; in another form of the invention, skewer 310 comprises a probe; and in another form of the invention, skewer 310 comprises a suture passer. Elongated hollow rod 305, skewer 310 and hollow plunger 315 are preferably sized so that hollow plunger 315 extends beyond the distal end of elongated hollow rod 305, and skewer 310 extends beyond the distal end of hollow plunger 315.

Figure 38:
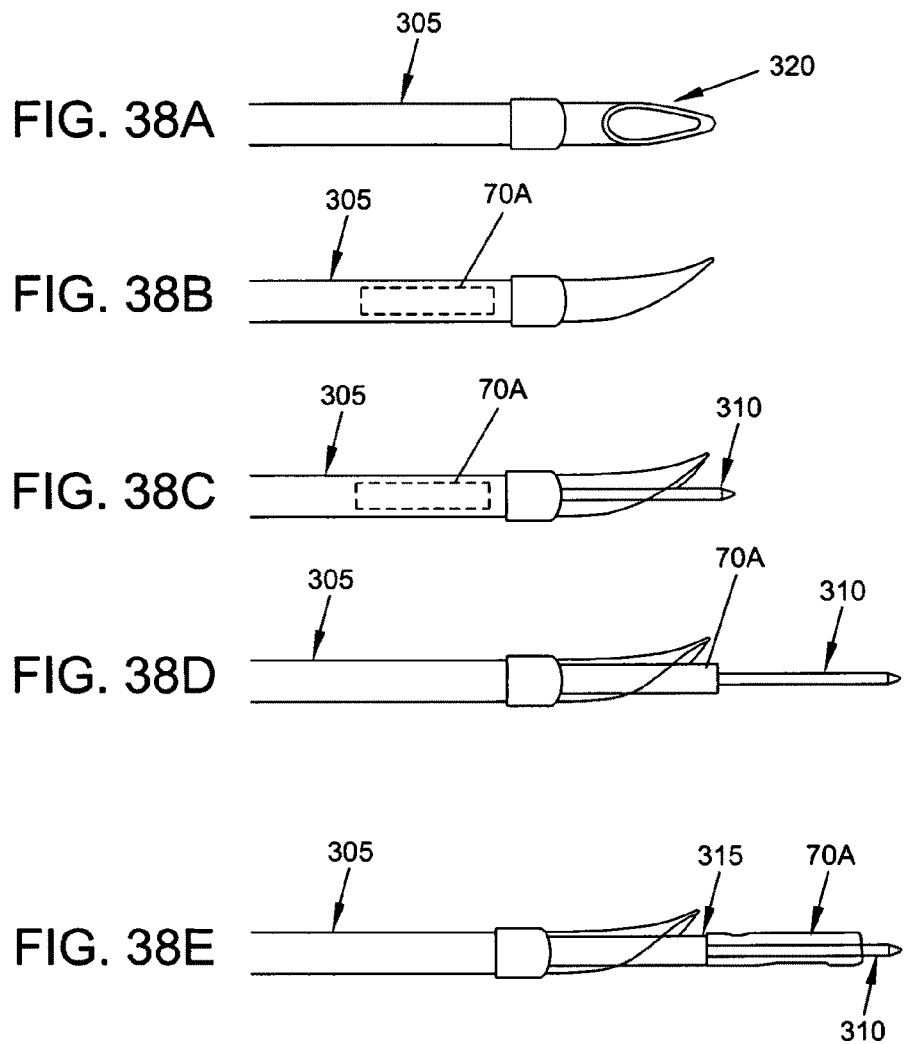
FIGS. 38A-38E are schematic views showing the apparatus of FIG. 37 being used to deliver fibrin clot to a site within the body.

In one preferred manner of use, and looking now at FIGS. 38A-38E, skewer 310 and hollow plunger 315 are retracted into the intermediate portion of elongated hollow rod 305 (FIG. 38A), and then elongated rod 305 is used to pick up a mass of fibrin clot within its interior (FIG. 38B). Next, skewer 310 is advanced out elongated hollow rod 305 (FIG. 38C), impaling the fibrin clot as the skewer advances. Skewer 310 is advanced into its extended position, and the distal tip of skewer 310 is positioned at the site where the fibrin clot is to be inserted. Then, hollow plunger 315 is advanced distally so as to force the fibrin clot to exit elongated rod 305, riding on skewer 310 (FIG. 38D). Finally, hollow plunger 315 is used to force the fibrin clot off skewer 310 and into the body (FIG. 38E).

Preferably, the distal end of elongated rod 305 of skewer-plunger 300 has a beveled, atraumatic tip 320 to protect cartilage, direct and/or manage the clot, dilate openings or tears, pack defects in the tissue, etc.

Figure 39:
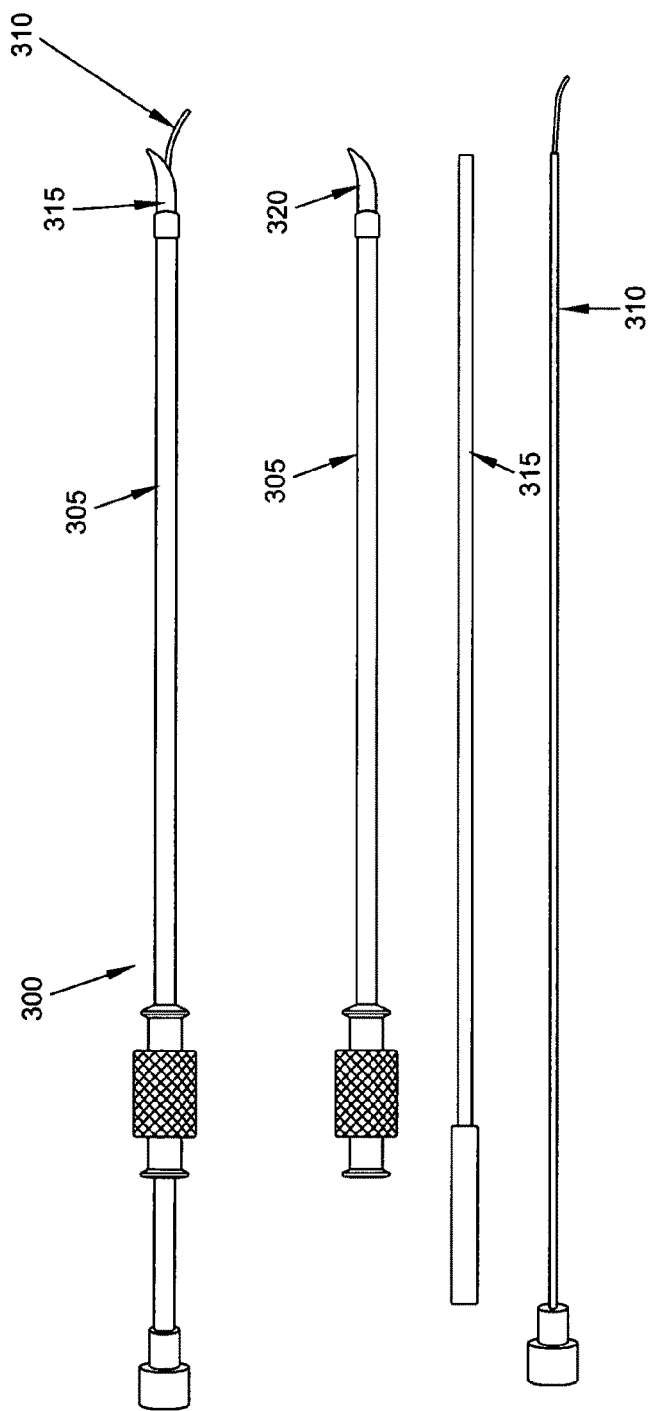
FIG. 39 is a schematic view showing other additional alternative apparatus which may be used to harvest and deliver a fibrin clot.

In one preferred form of the invention, skewer 310 may be formed out of stainless steel and, if desired, may be pre-bent or bent intraoperatively with custom bends so as to permit fibrin clot to be delivered to a hard to reach location. Alternatively, and looking now at FIG. 39, skewer 310 may be formed out of a superelastic material (e.g., a shape memory alloy such as Nitinol) and may be configured so that the distal end of the skewer has a curved configuration when it is in its unrestrained configuration. As a result, when the skewer 310 is advanced out of elongated hollow rod 305, the distal end of skewer 310 can have a different orientation that the major axis of elongated hollow rod 305, whereby to permit the fibrin clot to be delivered "off axis". Such a construction can be extremely helpful when the fibrin clot needs to be delivered into difficult-to-reach locations such as meniscal tears, rotator cuff tears, ACL graft-bone interfaces, etc. See, for example, FIG. 39 where the distal tip of skewer 310 is formed with a curved configuration.

MODIFICATIONS

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. Apparatus for extracting fibrin from blood so as to form a fibrin clot having its fibers oriented in a common direction, the apparatus comprising:
   a vessel for holding drawn blood;
   a lid for selectively closing off the vessel; and
   a precipitator connected to the lid for engaging the drawn blood contained within the vessel and acting as a focal point for the precipitation of fibrin clot, the precipitator being configured for constrained movement relative to the vessel so as to create a fibrin clot having its fibers oriented in a common direction.

2. Apparatus according to claim 1 wherein the precipitator comprises a rod.

3. Apparatus according to claim 2 wherein the rod is slidably connected to the lid.

4. Apparatus according to claim 3 wherein the rod is rotatable relative to the lid.

5. Apparatus according to claim 3 wherein the rod is radially slidably along to the lid.

6. Apparatus according to claim 3 wherein the rod is movable longitudinally relative to the lid.

7. Apparatus according to claim 2 wherein the lid is rotatable relative to the vessel.

8. Apparatus according to claim 2 wherein the distal end of the rod engages the bottom surface of the vessel.

9. Apparatus according to claim 2 wherein the distal end of the rod is spaced a small distance from the bottom surface of the vessel.

10. Apparatus according to claim 2 wherein the distal end of the rod is disposed just below the top surface of the drawn blood contained within the vessel.

11. Apparatus according to claim 2 wherein the rod comprises line markings.

12. Apparatus according to claim 2 wherein the vessel is transparent.

13. Apparatus according to claim 2 wherein the rod comprises frosted glass.

14. Apparatus according to claim 1 wherein the vessel is a syringe for drawing blood, the lid is a plunger movable along the syringe, and the precipitator is a rod along which the plunger moves.

15. Apparatus for cutting a segment of fibrin clot from a larger mass of fibrin clot and dispensing the cut segment of fibrin clot to a desired location, the apparatus comprising:
   a clot preparation block including a chamber for receiving a mass of fibrin clot; and
   a coring tube comprising:
      a hollow tube having a window formed therein; and
      an inner member having an open distal chamber aligned with the window;
      the hollow tube being sized to fit within the chamber of the clot preparation block.

16. Apparatus according to claim 15 wherein the hollow tube comprises an atraumatic distal tip.

17. Apparatus according to claim 15 wherein the window comprises a sharpened edge.

18. A method for forming a fibrin clot having its fibers oriented in a common direction, the method comprising:
   placing drawn blood in a vessel;
   mounting a precipitator to the vessel so that the precipitator extends into the drawn blood contained in the vessel, wherein the precipitator is configured for constrained movement relative to the vessel so as to create a fibrin clot having its fibers oriented in a common direction; and
   agitating the drawn blood so as to cause a fibrin clot to form.

19. A method for cutting a mass of fibrin clot from a larger mass of fibrin clot and dispensing the cut mass of fibrin clot to a desired location, the method comprising:
   providing apparatus comprising:
      a clot preparation block including a chamber for receiving a mass of fibrin clot;
      a coring tube sized to fit within the chamber of the clot preparation block; and a plunger for expelling a mass of fibrin clot from the coring tube;

positioning a mass of fibrin clot in the clot preparation block;

inserting the coring tube into the clot preparation block so as to load the mass of fibrin clot into the coring tube;

withdrawing the coring tube from the clot preparation block;

positioning the coring tube adjacent to a location at which the fibrin clot is to be dispensed;

actuating the plunger so as to expel the mass of fibrin clot at the selected location.

* * * * *